(12) United States Patent
Gaarde et al.

(10) Patent No.: US 7,709,630 B2
(45) Date of Patent: May 4, 2010

(54) ANTISENSE MODULATION OF CONNECTIVE TISSUE GROWTH FACTOR EXPRESSION

(75) Inventors: William Gaarde, Carlsbad, CA (US); Andrew T Watt, Oceanside, CA (US); Brett P Monia, Encinitas, CA (US); Mausumee Guha, Trabuco Canyon, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 245 days.

(21) Appl. No.: 12/011,761

(22) Filed: Jan. 28, 2008

(65) Prior Publication Data

US 2010/0035964 A1    Feb. 11, 2010

Related U.S. Application Data

(63) Continuation of application No. 10/946,914, filed on Sep. 21, 2004, now abandoned, which is a continuation-in-part of application No. 10/006,191, filed on Dec. 10, 2001, now Pat. No. 6,965,025.

(51) Int. Cl.
| | |
|---|---|
| C07H 21/04 | (2006.01) |
| C07H 21/02 | (2006.01) |
| A61K 31/70 | (2006.01) |
| C12Q 1/68 | (2006.01) |
| C12N 5/00 | (2006.01) |

(52) U.S. Cl. .............................. 536/24.5; 435/6; 514/44; 536/23.1; 536/24.1

(58) Field of Classification Search ....................... None
See application file for complete search history.

(56) References Cited

U.S. PATENT DOCUMENTS

| | | | |
|---|---|---|---|
| 5,585,270 | A | 12/1996 | Grotendorst et al. |
| 5,783,187 | A | 7/1998 | Grotendorst et al. |
| 5,876,730 | A | 3/1999 | Brigstock et al. |
| 5,998,148 | A | 12/1999 | Bennett et al. |
| 6,069,006 | A | 5/2000 | Grotendorst et al. |
| 6,150,101 | A | 11/2000 | Grotendorst et al. |
| 6,232,064 | B1 | 5/2001 | Grotendorst et al. |
| 6,358,741 | B1 | 3/2002 | Schmidt et al. |
| 6,965,025 | B2 | 11/2005 | Gaarde et al. |
| 2005/0059629 | A1 | 3/2005 | Gaarde et al. |

FOREIGN PATENT DOCUMENTS

| | | |
|---|---|---|
| EP | 02795724.0 | 9/2004 |
| WO | WO 99/66959 | 12/1999 |
| WO | WO 00/13706 | 3/2000 |
| WO | WO 00/27868 | 5/2000 |
| WO | WO 00/35936 | 6/2000 |
| WO | WO 01/29217 | 4/2001 |
| WO | WO 01/85941 | 11/2001 |

OTHER PUBLICATIONS

U.S. Appl. No. 11/985,843, filed Nov. 15, 2007, Gaarde et al.
Supplementary European Search Report issued Apr. 3, 2006 by the European Patent Office in connection in connection with PCT International Application No. PCT/US02/38618.
Communication Pursuant to Article 96(2) EPC issued Oct. 6, 2006, 2008 in connection with European Application No. EP027957240.
Communication Pursuant to Article 94(3) EPC issued May 28, 2008 in connection with European Application No. EP027957240.
Allawi, H.T. et al. (2001) "Mapping of RNA accessible sites by extension of random oligonucleotide libraries with reverse transcriptase," RNA, 7:314-327.
Ho, S.P. et al. (1998) "Mapping of RNA accessible sites for antisense experiments with oligonucleotide libraries," Nature Biotech., 16:59-63.
Matveeva, O. et al. (1997) A rapid in vitro method for obtaining RNA accessibility patterns for complementary DNA probes: correlation with an intracellular pattern and known.
Milner, N. et al. (1997) "Selecting effective antisense reagents on combinatorial oligonucleotide arrays," Nature Biotech., 15:537-541.
Patzel, V. et al. (1998) "Theoretical design of antisense RNA structures substantially improves annealing kinetics and efficacy in human cells," Nature Biotech., 16:64-68.
Patzel, V. et al. (1999) "A theoretical approach to select effective antisense oligodeoxyribonucleotides at high statistical probability," Nucleic Acids Res., 27:4328-4334.
Walton, S.P. et al. (1999) "Prediction of antisense oligonucleotide binding affinity to a structured RNA target," Biotechnology and Bioengineering, 65:1-9.
Adler et al. "Glomerular mRNAs in Human Type I Diabetis: Biochemical Evidence for Microalbuminuria as a manifestation of Diabetic Nephrology," Kidney International, 2001, pp. 2330-2336.
Allen et al., "Enhanced insulin-like growth factor binding protein-related protein 2 (Connective tissue growth factor) expression in patients with idiopathic pulmonary fibrosis and pulmonary sarcoidosis" Am. J. Respir. Cell Mol. Biol. 1999, 21:693-700.
Babic et al., "Fisp12/mouse connective tissue growth factor mediates endothelial cell adhesion and migration through integrin alphavbeta3, promotes endothelial cell survival, and induces angiogenesis in vivo," Mol. Cell Biol., 1999, 19:2958-2966.

(Continued)

Primary Examiner—Sean R McGarry
(74) Attorney, Agent, or Firm—John P. White; Cooper & Dunham LLP

(57) ABSTRACT

Antisense compounds, compositions and methods are provided for modulating the expression of connective tissue growth factor. The compositions comprise antisense compounds, particularly antisense oligonucleotides, targeted to nucleic acids encoding connective tissue growth factor. Methods of using these compounds for modulation of connective tissue growth factor expression and for treatment of diseases associated with expression of connective tissue growth factor are provided.

23 Claims, No Drawings

OTHER PUBLICATIONS

Boes et al., "Connective tissue growth factor (IGFBP-rP2) expression and regulation in cultured bovine endothelial cells," Endocrinology 1999 140:1575-1580.

Bradham et al., "Connective tissue growth factor: a cysteine-rich mitogen secreted by human vascular endothelial cells is related to the SRC-induced immediate early gene product CEF-10," J. Cell Biol., 1991, 114:1285-1294.

Duncan et al., "Connective tissue growth factor mediates transforming growth factor beta-induced collagen synthesis: down-regulation by cAMP," Faseb J., 1999, 13:1774-1786.

Hishikawa et al., "Transforming growth factor-beta (1) induces apoptosis via connective tissue growth factor in human aortic smooth muscle cells," Eyr. J. Pharmacol., 1999, 385:287-290.

Hishikawa et al., "Static pressure regulates connective tissue growth factor expression in human mesangial cells," J. Biol. Chem., 2001, 276:16797-16803.

Hishikawa et al., "Connective tissue growth factor induces apoptosis in human breast cancer cell line MCF-7," J. Biol. Chem., 1999, 274:37461-37466.

Ito et al., "Kinetics of connective tissue growth factor expression during experimental proliferative glomerulonephritis," J. Am. Soc. Nephrol., 2001, 12:472-484.

Jedsadayanmata et al., "Activation-dependent adhesion of human platelets of Cyr61 and Fisp12/mouse connective tissue growth factor is mediated through integrin alpha (IIB)beta(3)," J. Biol. Chem., 1999, 274:24321-24327.

Kasaragod et al., "Connective tissue growth factor expression in pediatric myofibroblastic tumors," Pediatr. Dev. Pathol., 2001, 4:37-45.

Kim et al., "Identification of a family of low-affinity insulin-like growth factor binding proteins (IGFBPs): characterization of connective tissue growth factor as a member of the IGFBP superfamily," Proc. Natl. Acad. Sci. USA., 1997, 94:12981-12986.

Kondo et al., "Characterization of a mouse ctgf 3'-UTR segment that mediates repressive regulation of gene expression," Biochem. Biophys. Res. Commun., 2000, 278:119-124.

Kothapalli et al., "Transforming growth factor beta induces anchorage-independent growth of NRK fibroblasts via a connective tissue growth factor-dependent signaling pathway," Cell Growth. Differ., 1997, 8:61-68.

Kubota et al., "Involvement of cis-acting repressive element(s) in the 3'-untranslated region of human connective tissue growth factor gene," FEBS Lett., 1999, 450:84-88.

Lasky et al., "Connective tissue growth factor mRNA expression is upregulated in bleomycin-induced lung fibrosis," Am. J. Physiol., 1998, 275:L365-371.

Lau et al., "The CCN family of angiogenic regulators: the integrin connection," Exp. Cell Res., 1999, 248:44-57.

Lopez-Bermejo et al., "Characterization of insulin-like growth factor-binding protein-related proteins (IGFBP-rPs) 1, 2, and 3 in human prostate epithelial cells:potential roles for IGFBP-rP1 and 2 in senescence of the prostatic epithelium," Endocrinology, 2000, 141:4072-4080.

Martinerie et al, "Physical mapping of human loci homologous to the chicken noc proto-oncogene," Oncogene, 1992, 7:2529-2534.

Moussad et al., Connective tissue growth factor: what's in a name?, Mol. Genet. Metab., 2000, 71:276-292.

Nakanishi et al., "Overexpression of connective tissue growth factor/hypertrophic chondrocyte-specific gene product 24 decreases bone density in adult mice and induces dwarfism," Biochem. Biophys. Res. Commun., 2001, 281:678-681.

Pereira et al., "transcriptional regulation of connective tissue growth factor by cortisol in osteoblasts," Am. J. Physiol. Endocrinol. Metab., 2000, 279:E570-576.

Riser et al., "Urinary CCN2 (CTGF) as a Possible Predictor of Diabetic Nephropathy: Preliminary Report," Kidney International, 2003, vol. 64, pp. 451-458.

Shimo et al., Inhibition of endogenous expression of connective tissue growth factor by its antisense oligonucleotide and antisense RNA suppresses proliferation and migration of vascular endothelial cells,: J. Biochem (Tokyo), 1998, 124:130-140.

Tsubaki et al., Effects of sodium butyrate on expression of members pf the IGF-binding protein superfamily in human mammary epithelial cells, J. Endocrinol., 2001, 169:97-110.

Twigg et al., "Advanced glycosylation end products up-regulate connective tissue growth factor (insulin-like growth factor-binding protein-related protein 2) in human fibroblasts: a potential mechanism for expansion of extracellular matrix in diabetes mellitus," Endocrinology, 2001, 142:1760-1769.

Vorwerk et al., "CTGF (IGFBP-rP2) is specifically expressed in malignant lymphoblasts of patients with acute lymphoblastic leukaemia (ALL)," Br. J. Cancer, 2000, 83:756-760.

Yang et al., "Identification of glycosylated 38-kDa connective tissue growth factor (IGFBP-related protein 2) and proteolytic fragments in human biological fluids, and up-regulation of IGFBP-rP2 expression by TGF-beta in Hs578T human breast cancer cells," J. Clin. Endocrinol. Metab., 1998, 83:2593-2596.

International Preliminary Examination Report issued Apr. 22, 2004 by the International Preliminary Examining Authority in connection with PCT International Application No. PCT/US02/38618.

International Search Report issued Dec. 24, 2003 by the International Searching Authority in connection with PCT International Application No. PCT/US02/38618.

Supplementary European Search Report issued Jun. 28, 2006 by the European Patent Office in connection in connection with PCT International Application No. PCT/US02/38618.

ANTISENSE MODULATION OF CONNECTIVE TISSUE GROWTH FACTOR EXPRESSION

CROSS REFERENCE TO RELATED APPLICATIONS

This application is a continuation of U.S. Ser. No. 10/946,914, filed Sep. 21, 2004 now abandoned, which is a continuation-is-part of U.S. Ser. No. 10/006,191, filed Dec. 10, 2001, now U.S. Pat. No. 6,965,025 B2, issued Nov. 15, 2005, the contents of each of which is hereby incorporated by reference in its entirety into the subject application.

FIELD OF THE INVENTION

The present invention provides compositions and methods for modulating the expression of connective tissue growth factor. In particular, this invention relates to compounds, particularly oligonucleotides, specifically hybridizable with nucleic acids encoding connective tissue growth factor. Such compounds have been shown to modulate the expression of connective tissue growth factor in cells and in vivo.

BACKGROUND OF THE INVENTION

In the course of studies of platelet-derived growth factor (PDGF) isoforms, a novel, cysteine-rich mitogenic peptide secreted by human vascular endothelial cells and related to the v-src-induced immediate early gene product CEF-10 was identified. An anti-PDGF antibody was used to screen a human umbilical vein endothelial cell (HUVEC) expression library, and the gene encoding this novel mitogen was named connective tissue growth factor (CTGF). The connective tissue growth factor protein was shown to stimulate DNA synthesis and promote chemotaxis of fibroblasts (Bradham et al., *J. Cell Biol.*, 1991, 114, 1285-1294).

Connective tissue growth factor (CTGF; also known as ctgrofact, fibroblast inducible secreted protein, fisp-12, NOV2, insulin-like growth factor-binding protein-related protein 2, IGFBP-rP2, IGFBP-8, HBGF-0.8, Hcs24, and ecogenin) is a member of the CCN(CTGF/CYR61/NOV) family of modular proteins, named for the first family members identified, connective tissue growth factor, cysteine-rich (CYR61), and nephroblastoma overexpressed (NOV), but the family also includes the proteins ELM-1 (expressed in low-metastatic cells), WISP-3 (Wnt-1-induced secreted protein), and COP-1 (WISP-2). CCN proteins have been found to be secreted, extracellular matrix-associated proteins that regulate cellular processes such as adhesion, migration, mitogenesis, differentiation, survival, angiogenesis, atherosclerosis, chondrogenesis, wound healing, tumorigenesis, and vascular and fibrotic diseases like scleroderma (Lau and Lam, *Exp. Cell Res.*, 1999, 248, 44-57).

In most cases, a single 2.4-kilobase connective tissue growth factor transcript has been reported in expression studies, although 3.5- and 7-kilobase transcripts have been reported in glioblastoma cells. Connective tissue growth factor is expressed in fibroblasts during normal differentiation processes that involve extracellular matrix (ECM) production and remodeling, such as embryogenesis and uterine decidualization following implantation. Connective tissue growth factor is also frequently overexpressed in fibrotic skin disorders such as systemic sclerosis, localized skin sclerosis, keloids, scar tissue, eosinophilic fasciitis, nodular fasciitis, and Dupuytren's contracture. Connective tissue growth factor mRNA or protein levels are elevated in fibrotic lesions of major organs and tissues including the liver, kidney, lung, cardiovascular system, pancreas, bowel, eye, and gingiva. In mammary, pancreatic and fibrohistiocytic tumors characterized by significant connective tissue involvement, connective tissue growth factor is overexpressed in the stromal compartment. In many cases, connective tissue growth factor expression is linked spatially and temporally to the profibrogenic cytokine transforming growth factor-beta (TGF-β) (Moussad and Brigstock, *Mol. Genet. Metab.*, 2000, 71, 276-292).

Connective tissue growth factor has been mapped to human chromosomal region 6q23.1, proximal to the c-myb gene, and chromosomal abnormalities involving this region have been associated with human tumors, such as Wilms' tumor (Martinerie et al., *Oncogene*, 1992, 7, 2529-2534).

Tumors with significant fibrotic and vascular components exhibit increased connective tissue growth factor expression, and connective tissue growth factor may be involved in the pathogenesis of pediatric myofibroblastic tumors. Of 12 pediatric tumors examined, all showed moderate to intense connective tissue growth factor expression in tumor cells and/or endothelial cells of the associated vasculature (Kasaragod et al., *Pediatr. Dev. Pathol.*, 2001, 4, 37-45).

Connective tissue growth factor mRNA is also specifically upregulated in malignant human leukemic lymphoblasts from children with acute lymphoblastic leukemia (ALL) (Vorwerk et al., *Br. J. Cancer*, 2000, 83, 756-760), and both mRNA and protein levels are upregulated by TGF-beta in Hs578T human breast cancer cells in a dose-dependent manner, indicating that connective tissue growth factor is an important neuroendocrine factor and a critical downstream effector of TGF-beta (Yang et al., *J. Clin. Endocrinol. Metab.*, 1998, 83, 2593-2596).

Based on a region of amino acid homology to insulin-like growth factor (IGF) binding proteins (IGFBPs), connective tissue growth factor was hypothesized to regulate cell growth through IGF. Recombinant human connective tissue growth factor was expressed in a baculoviral system and demonstrated to bind to IGF in vitro with low affinity, and thus, connective tissue growth factor was identified as a member of the IGFBP superfamily, and was given the name IGFBP-8 (Kim et al., *Proc. Natl. Acad. Sci. U.S.A.*, 1997, 94, 12981-12986).

The role of connective tissue growth factor has been investigated in a transgenic mouse. Transgenic mice overproducing the connective tissue growth factor protein under control of the collagen promoter could develop and their embryonic and neonatal growth were normal, but they displayed dwarfism within a few months of birth, bone density was decreased compared with normal mice, male testes were much smaller than normal and fertility was affected. These results indicate that the effects of overexpression of connective tissue growth factor affects endochondral ossification, and may also regulate embryonic development of the testes (Nakanishi et al., *Biochem. Biophys. Res. Commun.*, 2001, 281, 678-681).

In cultured 22-day fetal rat calvarial osteoblasts, cortisol stimulates transcription of connective tissue growth factor in a time- and dose-dependent manner, and cyclohexamide did not preclude this effect, indicating that this upregulation was not protein synthesis dependent. Glucocorticoids have complex effects on bone, some due to direct regulation of specific genes expressed by osteoblasts, and some indirect, mediated by locally produced growth factors or their binding proteins. IGFs have important stimulatory effects on bone formation, but glucocorticoids inhibit expression of IGFs. Because connective tissue growth factor binds to IGF, its increased expression could modulate the effect of cortisol on bone (Pereira et al., *Am. J. Physiol. Endocrinol. Metab.*, 2000, 279, E570-576).

Connective tissue growth factor may be regulated not only at the level of transcription, but also by proteolytic degradation, but this varies with cell type. In large vessel bovine endothelial cells, cyclic AMP (cAMP) was found to increase expression of intact connective tissue growth factor protein by inhibiting degradation, whereas TGF-beta stimulated neither mRNA nor protein levels. In microvessel cells, TGF-beta stimulates an increase in connective tissue growth factor mRNA and both TGF-beta and cAMP stimulated proteolytic degradation, and these differences may have an effect on angiogenesis and wound healing (Boes et al., *Endocrinology*, 1999, 140, 1575-1580).

Purified murine connective tissue growth factor promotes the adhesion of primary human dermal microvascular endothelial cells (HMVECs) and of platelets through integrin receptors $\alpha_v\beta_3$ and $\alpha_{IIb}\beta_3$, respectively, suggesting its involvement in cell adhesion signaling, hemostasis and thrombosis (Babic et al., *Mol. Cell. Biol.*, 1999, 19, 2958-2966; Jedsadayanmata et al., *J. Biol. Chem.*, 1999, 274, 24321-24327). Connective tissue growth factor also stimulates migration of HMVECs in culture through an integrin receptor $\alpha_3\beta_3$_ dependent mechanism. Furthermore, connective tissue growth factor can promote survival of HMVECs plated onto laminin but deprived of growth factors, a condition that otherwise induces apoptosis. In vivo, connective tissue growth factor induces neovascularization in rat corneal micropocket implants. Thus, connective tissue growth factor is an angiogenic inducer, and may play a role in adhesion, migration, and survival of endothelial cells during blood vessel growth, perhaps by delivering an antiapoptotic signal via its interaction with integrin $\alpha_v\beta_3$ (Babic et al., *Mol. Cell. Biol.*, 1999, 19, 2958-2966).

In contrast, connective tissue growth factor may negatively regulate growth of human prostate cells. Connective tissue growth factor expression is upregulated during senescence of normal human prostate epithelial cells (HPECs), and connective tissue growth factor is responsive to growth regulators such as all-trans retinoic acid (atRA), supporting a growth-regulatory role of connective tissue growth factor in prostatic epithelium (Lopez-Bermejo et al., *Endocrinology*, 2000, 141, 4072-4080).

Expansion of ECM with fibrosis occurs in many tissues as part of the end-organ complications of diabetes (i.e. diabetic nephropathy), and advanced glycosylation end products (AGE) are implicated as one causitive factor in diabetic tissue fibrosis. In addition to being a potent inducer of ECM synthesis and angiogenesis, connective tissue growth factor is increased in tissues from rodent models of diabetes. AGE treatment of primary cultures of CRL-2097 and CRL-1474 nonfetal human dermal fibroblasts resulted in an increase in steady state levels of connective tissue growth factor mRNA as well as protein levels in conditioned medium and cell-associated connective tissue growth factor, while other IGFBP-related proteins were not upregulated by AGE. Thus, AGE upregulates the profibrotic and proangiogenic protein connective tissue growth factor, which may play a role in diabetic complications (Twigg et al., *Endocrinology*, 2001, 142, 1760-1769).

Diabetic nephropathy is a syndrome occurring in people with diabetes mellitus and characterized by albuminuria, hypertension, and progressive renal insufficiency. Diabetic nephropathy is a common complication in patients with either type 1 or type 2 diabetes mellitus and is recognized to cause severe morbidity and mortality. Structural hallmarks of advanced diabetic nephropathy are glomerulosclerosis and tubulointerstitial fibrosis leading to kidney failure. Current therapies include ACE inhibitors and angiotensin II receptor blockers, both of which are not justified for blanket use among all newly diagnosed patients since only 30-40% will develop progressive renal disease and the long term side effects of these drugs are unknown.

In addition to the need for safe and effective treatments for diabetes is a need for a reliable method to accurately predict, at early stages of disease, which diabetic patients will develop nephropathy and progress to kidney failure. Persistent microalbuminuria is regarded as a predictor of established vascular damage and an indicator of incipient nephropathy. Studies of renal biopsies from patients with type 1 diabetic nephropathy demonstrate an increase in expression of CTGF in renal tissue exhibiting microalbuminuria and nephropathy, relative to normal control tissues (Adler et al., Kidney Int., 2001, 60, 2330-2336), suggesting CTGF is not only a mediator of diabetic nephropathy, but could be used as a marker for the development of disease (Riser et al., *Kidney Int.*, 2003, 64, 451-458).

In a murine lung fibrosis model, an increase in connective tissue growth factor mRNA expression is also induced by bleomycin, a known lung fibrogenic agent (Lasky et al., *Am. J. Physiol.*, 1998, 275, L365-371), as well as in bronchoalveolar lavage cells from patients with idiopathic pulmonary fibrosis and pulmonary sarcoidosis, in comparison to healthy nonsmoking control subjects, indicating that connective tissue growth factor is involved in the fibroproliferative response to injury (Allen et al., *Am. J. Respir. Cell Mol. Biol.*, 1999, 21, 693-700). Similarly, in an experimental model of proliferative glomerulonephritis, connective tissue growth factor mRNA expression was strongly increased in extracapillary and mesangial proliferative lesions and in areas of periglomerular fibrosis. The early glomerular connective tissue growth factor overexpression coincided with a striking upregulation of TGF-β proteins, and the kinetics of connective tissue growth factor expression strongly suggest a role in glomerular repair, possibly downstream of TGF-beta in this model of transient renal injury (Ito et al., *J. Am. Soc. Nephrol.*, 2001, 12, 472-484).

Disclosed and claimed in U.S. Pat. No. 5,876,730 is a substantially pure or isolated polypeptide characterized as having an amino acid sequence corresponding to the carboxy terminal amino acids of a connective tissue growth factor (CTGF) protein, wherein the polypeptide has an amino acid sequence beginning at amino acid residue 247 or 248 from the N-terminus of connective tissue growth factor, an isolated polynucleotide sequence encoding the connective tissue growth factor polypeptide, a recombinant expression vector which contains said polynucleotide, a host cell containing said expression vector, and a pharmaceutical composition comprising a therapeutically effective amount of connective tissue growth factor polypeptide in a pharmaceutically acceptable carrier. Antisense oligonucleotides are generally disclosed (Brigstock and Harding, 1999).

Disclosed and claimed in U.S. Pat. Nos. 5,783,187; 5,585,270; 6,232,064; 6,150,101; 6,069,006 and PCT Publication WO 00/35936 are an isolated polynucleotide encoding the connective tissue growth factor polypeptide, expression vectors, host cells stably transformed or transfected with said vectors; an isolated polynucleotide comprising 5' untranslated regulatory nucleotide sequences isolated from upstream of connective tissue growth factor, wherein said untranslated regulatory nucleotide sequences comprises a transcriptional and translational initiation region and wherein said sequence is a TGF-beta responsive element; an isolated nucleic acid construct comprising a non-coding regulatory sequence isolated upstream from a connective tissue growth factor (CTGF) gene, wherein said non-coding regulatory sequence is operably associated with a nucleic acid sequence which expresses a protein of interest or antisense RNA, wherein said nucleic acid sequence is heterologous to said non-coding sequence; and a fragment of connective tissue growth factor (CTGF) polypeptide having the ability to induce ECM synthesis, collagen synthesis and/or myofibroblast differentiation, comprising an amino acid sequence encoded by at least exon 2 or exon 3 of said polypeptide. Further claimed is a method for identifying a composition which affects TGF-beta-induced connective tissue growth factor expression, and a method of diagnosing a pathological state in a subject suspected of having a pathology selected from the group consisting of fibrotic disease and atherosclerosis, the method comprising obtaining a sample suspected of containing connective tissue growth factor, whereby detecting a difference in the level of connective tissue growth factor in the sample from the subject as compared to the level of connective tissue growth factor in the normal standard sample is diagnostic of a pathology characterized by a cell proliferative disorder associated with connective tissue growth factor in the subject. Further claimed is a method for ameliorating a cell proliferative disorder associated with connective tissue growth factor, comprising administering to a subject having said disorder, at the site of the disorder, a composition comprising a therapeutically effective amount of an antibody or fragment thereof that binds to connective tissue growth factor, wherein said antibody or fragment thereof does not bind to PDGF. Antisense oligonucleotides are generally disclosed (Grotendorst, 2000; Grotendorst and Bradham, 2001; Grotendorst and Bradham, 2000; Grotendorst and Bradham, 1996; Grotendorst and Bradham, 1998; Grotendorst and Bradham, 2000).

Disclosed and claimed in PCT Publication WO 99/66959 is a device for promoting neuronal regeneration, comprising a gene activated matrix comprising a biocompatible matrix and at least one neuronal therapeutic encoding agent having an operably linked promoter device, wherein the neuronal therapeutic encoding agent encodes an inhibitor of neuronal cell growth, and wherein the inhibitor of neuronal cell growth is selected from the group consisting of NFB42, TGF-beta, connective tissue growth factor (CTGF), and macrophage migration inhibitory factor (MIF), and wherein the neuronal therapeutic encoding agent is selected from the group consisting of a nucleic acid molecule, a vector, an antisense nucleic acid molecule and a ribozyme (Baird et al., 1999).

Disclosed and claimed in PCT Publication WO 00/27868 is a substantially pure connective tissue growth factor polypeptide or functional fragments thereof, an isolated polynucleotide sequence encoding said polypeptide, said polynucleotide sequence wherein T can also be U, a nucleic acid sequence complementary to said polynucleotide sequence, and fragments of said sequences that are at least 15 bases in length and that will hybridize to DNA which encodes the amino acid sequence of the connective tissue growth factor protein under moderate to highly stringent conditions. Further claimed is an expression vector including said polynucleotide, a host cell stably transformed with said vector, an antibody that binds to said polypeptide, and a method for producing said polypeptide. Further claimed is a method for inhibiting the expression of connective tissue growth factor in a cell comprising contacting the cell with a polynucleotide which binds to a target nucleic acid in the cell, wherein the polynucleotide inhibits the expression of connective tissue growth factor in the cell, wherein the polynucleotide is an antisense polynucleotide, as well as a kit for the detection of connective tissue growth factor expression comprising a carrier means being compartmentalized to receive one or more containers, comprising at least one container containing at least one antisense oligonucleotide that binds to connective tissue growth factor (Schmidt et al., 2000).

Disclosed and claimed in PCT Publication WO 00/13706 is a method for treating or preventing fibrosis, the method comprising administering to a subject in need an effective amount of an agent that modulates, regulates or inhibits the expression or activity of connective tissue growth factor or fragments thereof, and wherein the agent is an antibody, an antisense oligonucleotide, or a small molecule. The method is directed to treating kidney fibrosis and associated renal disorders, in particular, complications associated with diabetes and hypertension (Riser and Denichili, 2000).

Disclosed and claimed in PCT Publication WO 01/29217 is an isolated nucleic acid molecule comprising a nucleic acid sequence encoding a polypeptide comprising an amino acid sequence selected from a group comprising NOV1, NOV2 (connective tissue growth factor), and NOV3, a mature form or variant of an amino acid sequence selected from said group, as well as a nucleic acid molecule comprising a nucleic acid sequence encoding a polypeptide comprising an amino acid sequence selected from said group as well as mature and variant forms or fragments of said polypeptides, and the complement of said nucleic acid molecule. Antisense oligonucleotides are generally disclosed (Prayaga et al., 2001).

There are currently no known therapeutic agents that effectively inhibit the synthesis of connective tissue growth factor and to date, but investigative strategies aimed at modulating connective tissue growth factor function have involved the use of sodium butyrate (NaB), function blocking antibodies and antisense oligonucleotides.

NaB is a dietary micronutrient. Dietary factors are believed to play an important role in both the development and prevention of human cancers, including breast carcinoma. NaB is a major end product of digestion of dietary starch and fiber, and is a potent growth inhibitor that initiates cell differentiation of many cell types in vitro. NaB exerts its biological effects, in part, as a histone deacetylase inhibitor in mammary epithelial cells, induces apoptotic cell death in Hs578T estrogen-non-responsive human breast cancer cells, and can activate different genes involved in cell cycle arrest depending on cell type. NaB specifically upregulates the expression of connective tissue growth factor in a dose-dependent manner, stimulating an increase in both mRNA and protein levels in both cancerous and non-cancerous mammary cells (Tsubaki et al., *J. Endocrinol.*, 2001, 169, 97-110).

TGF-beta has the unique ability to stimulate growth of normal fibroblasts in soft agar, a property of transformed cells. Connective tissue growth factor cannot induce this anchorage-independent growth normal rat kidney (NRK) fibroblasts, but connective tissue growth factor synthesis and action are essential for TGF-β-induced anchorage-independence. Antibodies to connective tissue growth factor specifically blocked TGF-beta-induced anchorage-independent growth, and NRK fibroblasts transformed with a construct expressing the connective tissue growth factor gene in the antisense orientation were not responsive to TGF-beta in the anchorage-independent growth assay (Kothapalli et al., *Cell Growth. Differ.*, 1997, 8, 61-68). These CTGF-antisense expressing NRK cells were also used to show that TGF-beta-stimulated collagen synthesis is mediated by connective tissue growth factor, indicating that connective tissue growth factor may be a useful target for antifibrotic therapies (Duncan et al., *Faseb J.*, 1999, 13, 1774-1786).

The 3'-untranslated region (UTR) of the human connective tissue growth factor cDNA bears several consensus sequences for regulatory elements. When the 3'-UTR was fused downstream of a reporter gene, it was found to act as a strong cis-acting repressive element, and the antisense 3'-UTR had a similar, but stronger effect. (Kubota et al., *FEBS Lett.*, 1999, 450, 84-88). Comparison of the human and mouse connective tissue growth factor 3'-UTRs revealed a conserved small segment of 91 bases. This region was amplified by RT-PCR from NIH3T3 mouse fibroblasts and used to make a chimeric fusion construct for analysis of its repressive effects. The mouse connective tissue growth factor 3'-UTR in either the sense or the antisense orientation had a strong repressive effect on transcription of the reporter gene, indicating an orientation independence of this regulatory element (Kondo et al., *Biochem. Biophys. Res. Commun.*, 2000, 278, 119-124).

A phosphorothioate antisense oligonucleotide, 16 nucleotides in length and targeted to the translation initiation start site, was used to inhibit expression of connective tissue growth factor and suppress proliferation and migration of bovine aorta vascular endothelial cells in culture (Shimo et al., *J. Biochem.* (Tokyo), 1998, 124, 130-140). This antisense oligonucleotide was also used to show that connective tissue growth factor induces apoptosis in MCF-7 human breast cancer cells and that TGF-beta-induced apoptosis is mediated, in part, by connective tissue growth factor (Hishikawa et al., *J. Biol. Chem.*, 1999, 274, 37461-37466). The same antisense oligonucleotide was also found to inhibit the TGF-beta-mediated activation of caspase 3 and thus to inhibit induction of TGF-beta-mediated apoptosis in human aortic smooth muscle cells (HASC) (Hishikawa et al., *Eur. J. Pharmacol.*, 1999, 385, 287-290). This antisense oligonucleotide was also used to block connective tissue growth factor expression and demonstrate that high blood pressure upregulates expression of connective tissue growth factor in mesangial cells, which in turn enhances ECM protein production and induces apoptosis, contributing to the remodeling of mesangium and ultimately glomerulosclerosis (Hishikawa et al., *J. Biol. Chem.*, 2001, 276, 16797-16803).

Consequently, there remains a long felt need for additional agents capable of effectively inhibiting connective tissue growth factor function.

Antisense technology is emerging as an effective means for reducing the expression of specific gene products and may therefore prove to be uniquely useful in a number of therapeutic, diagnostic, and research applications for the modulation of connective tissue growth factor expression.

The present invention provides compositions and methods for modulating connective tissue growth factor expression in cells and in vivo.

SUMMARY OF THE INVENTION

The present invention is directed to compounds, particularly antisense oligonucleotides, which are targeted to a nucleic acid encoding connective tissue growth factor, and which modulate the expression of connective tissue growth factor. Pharmaceutical and other compositions comprising the compounds of the invention are also provided. Further provided are methods of modulating the expression of connective tissue growth factor in cells or tissues, comprising contacting said cells or tissues with one or more of the antisense compounds or compositions of the invention. Further provided are methods of treating an animal, particularly a human, suspected of having or being prone to a disease or condition associated with expression of connective tissue growth factor by administering a therapeutically or prophylactically effective amount of one or more of the antisense compounds or compositions of the invention. Also provided are methods of preventing or delaying the onset of diabetic nephropathy in animals, comprising administering an effective amount of one or more of the compounds or compositions of the invention. Methods of treating or delaying the onset of type 1 or type 2 diabetes in animals, comprising administering an effective amount of one or more of the compounds or compositions of the invention, are provided. Further provided are methods of inhibiting or preventing albuminuria and/or proteinuria in a diabetic animal by administering one or more compounds or compositions of the invention. Compounds and compositions comprising antisense oligonucleotides with a first region consisting of at least 5 contiguous 2'-deoxy nucleosides flanked by second and third regions, each of said second and third regions independently consisting of at least one 2'-O-methoxyethyl nucleoside, and wherein the internucleoside linkages of the first region are phosphorothioate linkages and the internucleoside linkages of the second and third regions are phosphodiester linkages, are also provided.

DETAILED DESCRIPTION OF THE INVENTION

The present invention employs oligomeric compounds, particularly antisense oligonucleotides, for use in modulating the function of nucleic acid molecules encoding connective tissue growth factor, ultimately modulating the amount of connective tissue growth factor produced. This is accomplished by providing antisense compounds which specifically hybridize with one or more nucleic acids encoding connective tissue growth factor. Oligomeric compounds that modulate the expression of connective tissue growth factor in cells or tissues are provided. It is shown herein that the oligomeric compounds of the invention prevent or delay the onset of type 1 and type diabetes in animal models of diabetes. The oligomeric compounds of the invention also are shown herein to prevent or delay the onset of diabetic nephropathy in diabetic animals and to prevent an increase in proteinuria and/or albuminuria in diabetic animals. These effects are achieved by contacting cells or tissues with the oligomeric compounds of the invention, or administering to an animal in need of treatment said compounds such that connective tissue growth factor expression is modulated, preferably inhibited.

The oligomeric compounds of the invention are chimeric oligonucleotides ("gapmers") with a central "gap" region consisting of 2'-deoxynucleotides, which is flanked on both sides by "wings" composed of 2'-methoxyethyl (2'-MOE) nucleotides. In one embodiment, the internucleoside (backbone) linkages of the chimeric compounds are phosphorothioate (P=S) throughout the oligonucleotide. In another embodiment, the chimeric compounds have phosphorothioate linkages in the central gap and phosphodiester linkages in the wings.

As used herein, the terms "target nucleic acid" and "nucleic acid encoding connective tissue growth factor" encompass DNA encoding connective tissue growth factor, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of connective tissue growth factor. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding connective tissue growth factor. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding connective tissue growth factor, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions. Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

The compounds of the present invention can also be applied in the areas of drug discovery and target validation. The present invention comprehends the use of the compounds and preferred target segments identified herein in drug discovery efforts to elucidate relationships that exist between CTGF and a disease state, phenotype, or condition. These methods include detecting or modulating CTGF comprising contacting a sample, tissue, cell, or organism with the compounds of the present invention, measuring the nucleic acid or protein level of CTGF and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (reviewed in (To, *Comb. Chem. High Throughput Screen*, 2000, 3, 235-41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

For therapeutics, an animal, preferably a human, suspected of having a disease or disorder which can be treated by modulating the expression of CTGF is treated by administering one or more antisense compounds in accordance with this invention. For example, in one non-limiting embodiment, the methods comprise the step of administering to the animal in need of treatment, a therapeutically effective amount of a CTGF inhibitor. The CTGF inhibitors of the present invention effectively inhibit the activity of the CTGF target protein or inhibit the expression of the CTGF protein. In one embodiment, the disease or disorder is diabetes, including type 1 and type 2 diabetes and complications arising therefrom.

The compounds of the invention can be utilized in pharmaceutical compositions by adding an effective amount of a compound to a suitable pharmaceutically acceptable diluent or carrier. Use of the compounds and methods of the invention may also be useful prophylactically.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O—dimethylaminoethoxyethyl or 2'-DMAEOE), i.e., 2'-O—CH$_2$—O—CH$_2$—N(CH$_3$)$_2$ also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-5-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of connective tissue growth factor is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding connective tissue growth factor, enabling sandwich and other assays to easily be constructed to exploit this fact. Hybridization of the antisense oligonucleotides of the invention with a nucleic acid encoding connective tissue growth factor can be detected by means known in the art. Such means may include conjugation of an enzyme to the oligonucleotide, radiolabelling of the oligonucleotide or any other suitable detection means. Kits using such detection means for detecting the level of connective tissue growth factor in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. Nos. 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint.

(Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p. 92; Muranishi, *Critical Reviews in Therapeutic Drug Carrier Systems,* 1990, 7, 1-33; El Hariri et al., *J. Pharm. Pharmacol.,* 1992, 44, 651-654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1-33; Yamamoto et al., *J. Pharm. Exp. Ther.,* 1992, 263, 25; Yamashita et al., *J. Pharm. Sci.,* 1990, 79, 579-583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, page 92; Muranishi, *Critical Reviews in Therapeutic Drug Carrier Systems,* 1990, 7, 1-33; Buur et al., *J. Control Rel.,* 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1-33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., *Antisense Res. Dev.,* 1995, 5, 115-121; Takakura et al., *Antisense & Nucl. Acid Drug Dev.,* 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.0001 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.0001 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., Nucleic Acids Research, 1993, 21, 3197-3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.*, 1993, 36, 831-841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3' phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486-504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH, gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-0-(dimethylaminooxyethyl) nucleoside amidites

2'-(Dimethylaminooxyethoxy) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC(Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O—[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O—[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O—[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetra-hydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_2OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum ((Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HuVEC Cells:

The human umbilical vein endothilial cell line HuVEC was obtained from the American Type Culture Collection (Manassas, Va.). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Connective Tissue Growth Factor Expression Antisense modulation of connective tissue growth factor expression can be assayed in a variety of ways known in the art. For example, connective tissue growth factor mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of connective tissue growth factor can be quantitated in a variety of ways well known in the art, such as immunoprecipitation, Western blot analysis (immunoblotting), ELISA or fluorescence-activated cell sorting (FACS). Antibodies directed to connective tissue growth factor can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758-1764. Other methods for poly (A)+ mRNA isolation are taught in, for example, Ausubel, F. M. et al., *Current Protocols in Molecular Biology*, Volume 1, pp. 4.5.1-4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 µL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Connective Tissue Growth Factor mRNA Levels Quantitation of connective tissue growth factor mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM, obtained from either Operon Technologies Inc., Alameda, Calif. or Integrated DNA Technologies Inc., Coralville, Iowa) is attached to the 5' end of the probe and a quencher dye (e.g., TAMRA, obtained from either Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen, Carlsbad, Calif. RT-PCR reactions were carried out by adding 20 µL PCR cocktail (2.5×PCR buffer (—MgCl2), 6.6 mM MgCl2, 375 µm each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96 well plates containing 30 µL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, Analytical Biochemistry, 1998, 265, 368-374.

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 480 nm and emission at 520 nm.

Probes and primers to human connective tissue growth factor were designed to hybridize to a human connective tissue growth factor sequence, using published sequence information (GenBank accession number M92934.1, incorporated herein as SEQ ID NO:3). For human connective tissue growth factor the PCR primers were:

forward primer: ACAAGGGCCTCTTCTGTGACTT (SEQ ID NO: 4)

reverse primer: GGTACACCGTACCACCGAAGAT (SEQ ID NO: 5) and the PCR probe was: FAM-TGTGCACCGC-CAAAGATGGTGCT-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer: GAAGGTGAAGGTCGGAGTC(SEQ ID NO:7)

reverse primer: GAAGATGGTGATGGGATTTC (SEQ ID NO:8) and the PCR probe was: 5' JOE-CAAGCTTCCCGT-TCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse connective tissue growth factor were designed to hybridize to a mouse connective tissue growth factor sequence, using published sequence information (GenBank accession number BC006783.1, incorporated herein as SEQ ID NO:10). For mouse connective tissue growth factor the PCR primers were:

forward primer: GGCAAATTCAACGGCACAGT (SEQ ID NO:11)

reverse primer: GCCCCCCACCCCAAA (SEQ ID NO: 12) and the PCR probe was: FAM-TCATAATCAAAGAAG-CAGCAAGCACTTCCTG-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye.

For mouse GAPDH the PCR primers were:

forward primer: GGCAAATTCAACGGCACAGT(SEQ ID NO:14)

reverse primer: GGGTCTCGCTCCTGGAAGAT(SEQ ID NO:15) and the PCR probe was: 5' JOE-AAGGC-CGAGAATGGGAAGCTTGTCATC-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Connective Tissue Growth Factor mRNA Levels

Eighteen Hours after Antisense Treatment, Cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human connective tissue growth factor, a human connective tissue growth factor specific probe was prepared by PCR using the forward primer ACAAGGGCCTCTTCT-GTGACTT (SEQ ID NO: 4) and the reverse primer GGTA-CACCGTACCACCGAAGAT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse connective tissue growth factor, a mouse connective tissue growth factor specific probe was prepared by PCR using the forward primer GCTCAGGGTAAGGTC-CGATTC (SEQ ID NO: 11) and the reverse primer GCCCCCCACCCCAAA (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Connective Tissue Growth Factor Expression by Chimeric Phosphorothioate Oligonucleotides Having 2'-Moe Wings and a Deoxy Gap In accordance with the present invention, a series of oligonucleotides were designed to target different regions of the human connective tissue growth factor RNA, using published sequences (GenBank accession number M92934.1, incorporated herein as SEQ ID NO: 3, GenBank accession number X78947.1, incorporated herein as SEQ ID NO: 17, GenBank accession number XM_037055.1, incorporated herein as SEQ ID NO: 18, and GenBank accession number XM_037056.1, incorporated herein as SEQ ID NO: 19). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human connective tissue growth factor mRNA levels by quantitative real-time PCR as described in other examples herein. Data are averages from two experiments. If present, "N.D." indicates "no data".

TABLE 1

Inhibition of human connective tissue growth factor mRNA
levels by chimeric phosphorothioate oligonucleotides having
2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 100880 | Coding | 3 | 707 | gcagttggctctaatcatag | 0 | 20 |
| 100883 | Coding | 3 | 828 | tgaccatgcacaggcggctc | 12 | 21 |
| 100885 | Coding | 3 | 917 | ctcaaacttgataggcttgg | 18 | 22 |
| 100886 | Coding | 3 | 956 | tttagctcggtatgtcttca | 0 | 23 |
| 100888 | Coding | 3 | 1028 | cttgaactccaccggcaggg | 28 | 24 |
| 100889 | Coding | 3 | 1076 | ggtcttgatgaacatcatgt | 40 | 25 |
| 100890 | Coding | 3 | 1098 | dacagttgtaatggcaggca | 23 | 26 |
| 100891 | Coding | 3 | 1147 | ccgtacatcttcctgtagta | 31 | 27 |
| 124173 | Coding | 18 | 304 | ccagctgcttggcgcagacg | 80 | 28 |
| 124183 | Coding | 18 | 718 | tctggaccaggcagttggct | 12 | 29 |
| 124184 | Coding | 18 | 723 | tgtggtctggaccaggcagt | 1 | 30 |
| 124185 | Coding | 18 | 728 | cactctgtggtctggaccag | 16 | 31 |
| 124188 | Coding | 18 | 882 | gatgcacttttgcccttct | 0 | 32 |
| 124189 | Coding | 18 | 927 | gccagaaagctcaaacttga | 77 | 33 |
| 124190 | Coding | 18 | 932 | gtgcagccagaaagctcaaa | 37 | 34 |
| 124196 | Coding | 18 | 1079 | caggtcttgatgaacatcat | 33 | 35 |
| 124197 | Coding | 18 | 1084 | aggcacaggtcttgatgaac | 53 | 36 |
| 124198 | Coding | 18 | 1089 | atggcaggcacaggtcttga | 9 | 37 |
| 124199 | Coding | 18 | 1098 | acagttgtaatggcaggcac | 72 | 38 |
| 124212 | 3'UTR | 18 | 1707 | ccacaagctgtccagtctaa | 66 | 39 |
| 124213 | 3'UTR | 18 | 1712 | acttgccacaagctgtccag | 1 | 40 |
| 124215 | 3'UTR | 18 | 1815 | ttaacttagataactgtaca | 79 | 41 |
| 124216 | 3'UTR | 18 | 1820 | ttaaattaacttagataact | 0 | 42 |
| 124230 | 3'UTR | 19 | 2098 | ttaataaaggccatttgttc | 0 | 43 |
| 124234 | 3'UTR | 19 | 2198 | cactctcaacaaataaactg | 14 | 44 |
| 124235 | 3'UTR | 19 | 2203 | ggtcacactctcaacaaata | 87 | 45 |
| 124236 | 3'UTR | 19 | 2208 | cttttggtcacactctcaac | 35 | 46 |
| 124237 | 3'UTR | 19 | 2213 | tgtaacttttggtcacactc | 35 | 47 |
| 124238 | 3'UTR | 19 | 2218 | aaacatgtaacttttggtca | 89 | 48 |
| 124239 | 3'UTR | 19 | 2242 | ctttattttcaactagaaag | 0 | 49 |
| 144294 | Coding | 18 | 303 | cagctgcttggcgcagacgc | 30 | 50 |
| 144305 | Coding | 18 | 622 | ccttgggctcgtcacacacc | 0 | 51 |
| 144311 | Coding | 18 | 725 | tctgtggtctggaccaggca | 49 | 52 |
| 144314 | Coding | 18 | 929 | cagccagaaagctcaaactt | 0 | 53 |
| 144315 | Coding | 18 | 935 | ctggtgcagccagaaagctc | 0 | 54 |
| 144319 | Coding | 18 | 1080 | acaggtcttgatgaacatca | 0 | 55 |

TABLE 1-continued

Inhibition of human connective tissue growth factor mRNA
levels by chimeric phosphorothioate oligonucleotides having
2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 144320 | Coding | 18 | 1086 | gcaggcacaggtcttgatga | 0 | 56 |
| 144321 | Coding | 18 | 1091 | taatggcaggcacaggtctt | 0 | 57 |
| 144323 | Coding | 18 | 1156 | ccatgtctccgtacatcttc | 28 | 58 |
| 144336 | 3'UTR | 18 | 1711 | cttgccacaagctgtccagt | 1 | 59 |
| 144337 | 3'UTR | 18 | 1740 | aaaaatctggcttgttacag | 0 | 60 |
| 144338 | 3'UTR | 18 | 1822 | ctttaaattaacttagataa | 0 | 61 |
| 144345 | 3'UTR | 19 | 2206 | tttggtcacactctcaacaa | 38 | 62 |
| 144346 | 3'UTR | 19 | 2212 | gtaacttttggtcacactct | 36 | 63 |
| 144347 | 3'UTR | 19 | 2219 | caaacatgtaacttttggtc | 24 | 64 |
| 144348 | 3'UTR | 19 | 2243 | actttattttcaactagaaa | 0 | 65 |
| 144802 | Start Codon | 3 | 120 | cggcggtcatggttggcact | 0 | 66 |
| 144803 | Start Codon | 3 | 130 | cccatactggcggcggtcat | 0 | 67 |
| 144804 | Coding | 17 | 284 | ccgtccagcacgaggctcac | 49 | 68 |
| 144805 | Coding | 17 | 367 | agaggcccttgtgcgggtcg | 0 | 69 |
| 144806 | Coding | 17 | 383 | gagccgaagtcacagaagag | 68 | 70 |
| 144807 | Coding | 17 | 473 | aaggactctccgctgcggta | 0 | 71 |
| 144808 | Coding | 3 | 487 | cacgtgcactggtacttgca | 45 | 72 |
| 144809 | Coding | 17 | 611 | tcgcagcatttcccgggcag | 79 | 73 |
| 144810 | Coding | 17 | 615 | ctcctcgcagcatttcccgg | 7 | 74 |
| 144811 | Coding | 17 | 633 | gggctcgtcacacacccact | 17 | 75 |
| 144812 | Coding | 17 | 699 | gtctgggccaaacgtgtctt | 0 | 76 |
| 144813 | Coding | 3 | 698 | tctaatcatagttgggtctg | 6 | 77 |
| 144814 | Coding | 17 | 729 | gaccaggcagttggctctaa | 0 | 78 |
| 144815 | Coding | 17 | 819 | ctctagcctgcaggaggcgt | 0 | 79 |
| 144816 | Coding | 17 | 875 | atgttctcttccaggtcagc | 0 | 80 |
| 144817 | Coding | 17 | 915 | ggagattttgggagtacgga | 51 | 81 |
| 144818 | Coding | 17 | 926 | ttgataggcttggagatttt | 1 | 82 |
| 144820 | Coding | 17 | 979 | cacagaatttagctcggtat | 0 | 83 |
| 144822 | Coding | 3 | 981 | ggccgtcggtacatactcca | 0 | 84 |
| 144824 | Coding | 17 | 1037 | tccaccggcagggtggtggt | 16 | 85 |
| 144826 | Coding | 17 | 1051 | cagggcacttgaactccacc | 41 | 86 |
| 144828 | Coding | 17 | 1055 | ccgtcagggcacttgaactc | 0 | 87 |
| 144830 | Coding | 17 | 1115 | ggacagttgtaatggcaggc | 39 | 88 |
| 144833 | Coding | 17 | 1149 | gtagtacagcgattcaaaga | 13 | 89 |
| 144835 | Stop Codon | 3 | 1167 | tctggcttcatgccatgtct | 37 | 90 |

TABLE 1-continued

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 144837 | Stop Codon | 3 | 1177 | tctctcactctctggcttca | 25 | 91 |
| 144839 | 3'UTR | 3 | 1229 | tacggaaaaatgagatgtga | 41 | 92 |
| 144841 | 3'UTR | 3 | 1261 | atttaaataacttgtgctac | 0 | 93 |
| 144843 | 3'UTR | 3 | 1358 | ttcttcaaaccagtgtctgg | 0 | 94 |
| 144845 | 3'UTR | 3 | 1537 | cagtgagcacgctaaaattt | 72 | 95 |
| 144847 | 3'UTR | 3 | 1621 | gttctgacttaaggaacaac | 0 | 96 |
| 144849 | 3'UTR | 3 | 1697 | gctgtccagtctaatcgaca | 52 | 97 |

As shown in Table 1, SEQ ID NOs 24, 25, 27, 28, 33, 34, 35, 36, 38, 39, 41, 45, 46, 47, 48, 50, 52, 58, 62, 63, 64, 68, 70, 72, 73, 81, 86, 88, 90, 91, 92, 95 and 97 demonstrated at least 24% inhibition of human connective tissue growth factor expression in this assay and are therefore preferred. The target sites to which these preferred sequences are complementary are herein referred to as "active sites" and are therefore preferred sites for targeting by compounds of the present invention.

Example 16

Antisense Inhibition of Mouse Connective Tissue Growth Factor Expression by Chimeric Phosphorothioate Oligonucleotides Having 2'-Moe Wings and a Deoxy Gap In accordance with the present invention, a second series of oligonucleotides were designed to target different regions of the mouse connective tissue growth factor RNA, using published sequences (GenBank accession number BC006783.1, incorporated herein as SEQ ID NO: 10, and GenBank accession number M80263.1, incorporated herein as SEQ ID NO: 98). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse connective tissue growth factor mRNA levels by quantitative real-time PCR as described in other examples herein. Data are averages from two experiments. If present, "N.D." indicates "no data".

TABLE 2

Inhibition of mouse connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 100891 | Coding | 10 | 1220 | ccgtacatcttcctgtagta | 78 | 27 |
| 124173 | Coding | 98 | 374 | ccagctgcttggcgcagacg | 15 | 28 |
| 124183 | Coding | 98 | 788 | tctggaccaggcagttggct | 23 | 29 |
| 124184 | Coding | 98 | 793 | tgtggtctggaccaggcagt | 24 | 30 |
| 124185 | Coding | 98 | 798 | cactctgtggtctggaccag | 41 | 31 |
| 124188 | Coding | 98 | 952 | gatgcacttttgcccttct | 25 | 32 |
| 124189 | Coding | 98 | 997 | gccagaaagctcaaacttga | 79 | 33 |
| 124190 | Coding | 98 | 1002 | gtgcagccagaaagctcaa- | 72 | 34 |
| 124196 | Coding | 98 | 1149 | caggtcttgatgaacatcat | 12 | 35 |
| 124197 | Coding | 98 | 1154 | aggcacaggtcttgatgaac | 0 | 36 |

TABLE 2-continued

Inhibition of mouse connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 124198 | Coding | 98 | 1159 | atggcaggcacaggtcttga | 32 | 37 |
| 124199 | Coding | 98 | 1168 | acagttgtaatggcaggcac | 37 | 38 |
| 124212 | 3'UTR | 98 | 1774 | ccacaagctgtccagtctaa | 80 | 39 |
| 124213 | 3'UTR | 98 | 1779 | acttgccacaagctgtccag | 52 | 40 |
| 124215 | 3'UTR | 98 | 1874 | ttaacttagataactgtaca | 54 | 41 |
| 124216 | 3'UTR | 98 | 1879 | ttaaattaacttagataact | 24 | 42 |
| 124230 | 3'UTR | 98 | 2131 | ttaataaaggccatttgttc | 3 | 43 |
| 124234 | 3'UTR | 98 | 2235 | cactctcaacaaataaactg | 18 | 44 |
| 124235 | 3'UTR | 98 | 2240 | ggtcacactctcaacaaata | 16 | 45 |
| 124236 | 3'UTR | 98 | 2245 | cttttggtcacactctcaac | 0 | 46 |
| 124237 | 3'UTR | 98 | 2250 | tgtaacttttggtcacactc | 57 | 47 |
| 124238 | 3'UTR | 98 | 2255 | aaacatgtaacttttggtca | 36 | 48 |
| 124239 | 3'UTR | 98 | 2278 | ctttattttcaactagaaag | 0 | 49 |
| 100884 | Coding | 10 | 949 | acttttttgcccttcttaatg | 14 | 99 |
| 124165 | 5'UTR | 98 | 88 | gacgctccaggcggtggcgt | 0 | 100 |
| 124166 | 5'UTR | 98 | 93 | gtctggacgctccaggcggt | 0 | 101 |
| 124167 | 5'UTR | 98 | 131 | cggctggagcctggattcgg | 23 | 102 |
| 124168 | 5'UTR | 98 | 139 | gagaggcgcggctggagcct | 43 | 103 |
| 124169 | 5'UTR | 98 | 177 | acgcggtaggaggatgcaca | 24 | 104 |
| 124170 | Start Codon | 98 | 195 | gaggcgagcatgatcgggac | 0 | 105 |
| 124171 | Coding | 98 | 364 | ggcgcagacgcggcagcagc | 68 | 106 |
| 124172 | Coding | 98 | 369 | tgcttggcgcagacgcggca | 0 | 107 |
| 124174 | Coding | 98 | 418 | gcccttgtgtgggtcgcagg | 42 | 108 |
| 124175 | Coding | 98 | 431 | aatcgcagaagaggcccttg | 1 | 109 |
| 124176 | Coding | 98 | 507 | accgacccaccgaagacaca | 45 | 110 |
| 124177 | Coding | 98 | 550 | ttggtatttgcagctgcttt | 34 | 111 |
| 124178 | Coding | 98 | 583 | cacgcagcccacggcccca~ | 0 | 112 |
| 124179 | Coding | 98 | 605 | gcacgtccatgctgcatagg | 18 | 113 |
| 124180 | Coding | 98 | 650 | gcagcttgacccttctcggg | 20 | 114 |
| 124181 | Coding | 98 | 705 | actgctgtgcggtccttggg | 12 | 115 |
| 124182 | Coding | 98 | 741 | gtgtcttccagtcggtaggc | 60 | 116 |
| 124186 | Coding | 98 | 861 | aaggtattgtcattggtaac | 37 | 117 |
| 124187 | Coding | 98 | 884 | ggctctgcttctccagtctg | 5 | 118 |
| 124191 | Coding | 98 | 1013 | tcttcacactggtgcagcca | 0 | 119 |
| 124192 | Coding | 98 | 1049 | cgtctgtgcacaccccgcag | 31 | 120 |

TABLE 2-continued

Inhibition of mouse connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 124193 | Coding | 10 | 1068 | cggtgtgcagcagcggccgt | 5 | 121 |
| 124194 | Coding | 98 | 1092 | tccactggcagagtggtggt | 47 | 122 |
| 124195 | Coding | 98 | 1135 | catcatattctttttcatga | 1 | 123 |
| 124200 | Coding | 98 | 1183 | gtcattgtccccaggacagt | 33 | 124 |
| 124201 | Stop Codon | 98 | 1239 | tcctggctttacgccatgtc | 13 | 125 |
| 124202 | 3'UTR | 98 | 1293 | aaatgagatgcaactcagtt | 28 | 126 |
| 124203 | 3'UTR | 98 | 1487 | tcagtgtgcgttctggcact | 38 | 127 |
| 124204 | 3'UTR | 98 | 1504 | gttccaggagactcacctca | 54 | 128 |
| 124205 | 3'UTR | 98 | 1512 | tctccactgttccaggagac | 1 | 129 |
| 124206 | 3'UTR | 98 | 1522 | tctcctggcatctccactgt | 38 | 130 |
| 124207 | 3'UTR | 98 | 1528 | tttctttctcctggcatctc | 0 | 131 |
| 124208 | 3'UTR | 98 | 1594 | tccccggttacactccaaaa | 0 | 132 |
| 124209 | 3'UTR | 98 | 1625 | aggtctgtctgcaagcatgc | 0 | 133 |
| 124210 | 3'UTR | 98 | 1645 | tgctcagctctcgctagagc | 45 | 134 |
| 124211 | 3'UTR | 98 | 1730 | agtgtcactggaatcagaat | 47 | 135 |
| 124214 | 3'UTR | 98 | 1856 | caaatatatatatatatata | 42 | 136 |
| 124217 | 3'UTR | 98 | 1902 | acttaaaacaaaaacaaatg | 0 | 137 |
| 124218 | 3'UTR | 98 | 1927 | gctatcagtttaaaatccca | 42 | 138 |
| 124219 | 3'UTR | 98 | 1957 | gtgtcctacctatggtgttt | 48 | 139 |
| 124220 | 3'UTR | 98 | 1978 | tttgaatcacagataagctt | 48 | 140 |
| 124221 | 3'UTR | 98 | 1993 | cagtatctcctttgttttga | 34 | 141 |
| 124222 | 3'UTR | 98 | 2003 | attcccactgcagtatctcc | 44 | 142 |
| 124223 | 3'UTR | 98 | 2012 | caggtcacaattcccactgc | 30 | 143 |
| 124224 | 3'UTR | 98 | 2028 | ctgacagagagtcactcagg | 40 | 144 |
| 124225 | 3'UTR | 98 | 2058 | gctttatcacctgcacagca | 74 | 145 |
| 124226 | 3'UTR | 98 | 2064 | tacatagctttatcacctgc | 56 | 146 |
| 124227 | 3'UTR | 98 | 2071 | cttccaatacatagctttat | 66 | 147 |
| 124228 | 3'UTR | 98 | 2076 | tctgacttccaatacatagc | 18 | 148 |
| 124229 | 3'UTR | 98 | 2119 | atttgttcaccaacagggat | 0 | 149 |
| 124231 | 3'UTR | 98 | 2152 | ttaccctgagccagccattt | 14 | 150 |
| 124232 | 3'UTR | 98 | 2188 | aagaagcagcaagcacttcc | 40 | 151 |
| 124233 | 3'UTR | 98 | 2200 | cagtcataatcaaagaagca | 1 | 152 |
| 124240 | 3'UTR | 98 | 2283 | atatactttatttcaacta | 51 | 153 |

As shown in Table 2, SEQ ID NOs 27, 30, 31, 32, 33, 34, 37, 38, 39, 40, 41, 42, 47, 48, 103, 104, 106, 108, 110, 111, 116, 117, 120, 122, 124, 126, 127, 128, 130, 134, 135, 136, 138, 139, 140, 141, 142, 143, 144, 145, 146, 147, 151 and 153 demonstrated at least 24% inhibition of mouse connective tissue growth factor expression in this experiment and are therefore preferred. The target sites to which these preferred sequences are complementary are herein referred to as "active sites" and are therefore preferred sites for targeting by compounds of the present invention.

Example 17

Western Blot Analysis of Connective Tissue Growth Factor Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to connective tissue growth factor is used, with a radiolabelled or fluorescently labeled secondary antibody directed against the primary antibody species. Bands are visualized using a PHOSPHORIMAGER™ (Molecular Dynamics, Sunnyvale Calif.).

Example 18

Antisense Inhibition of Connective Tissue Growth Factor in a Murine Model of Type 1 Diabetes The Animal Models of Diabetic Complications Consortium (AMDCC) has developed protocols for the induction of diabetes in a number of animal models. The streptozotocin (STZ) induced diabetic model has been approved by the AMDCC as an appropriate model system for studies of diabetic nephropathy associated with type 1 diabetes. In accordance with the present invention, oligomeric compounds of the present invention were tested in the STZ-induced model of type 1 diabetes.

C57/BL6 mice received intraperitoneal injections of STZ daily for five days at a dose of 50 mg/kg. Blood chemistry was monitored on days 9, 10 and 11 and urine chemistry was monitored on days 13 and 14. Starting on day 14, diabetic mice were given subcutaneous injections of antisense oligonucleotide ISIS 124212 (SEQ ID NO: 39) twice a week for four months (days 14-134) at a dose of 20 mg/kg. Blood and urine chemistries were again monitored at days 104, 134 and 136. Non-diabetic (no induction with STZ) and saline-injected animals served as controls.

ISIS 124212 (SEQ ID NO: 39) is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

Following four months of oligonucleotide treatment, mice were sacrificed and mRNA expression levels of CTGF were determined in four different treatment groups: non-diabetic mice injected with saline, non-diabetic mice treated with antisense oligonucleotide, STZ-induced diabetic mice injected with saline and STZ-induced diabetic mice treated with antisense oligonucleotide.

CTGF target mRNA levels were determined by semiquantitative RT-PCR according to standard procedures. PCR results were normalized to the ubiquitously expressed mouse 18S gene. Probes and primers to mouse CTGF were designed to hybridize to mouse CTGF sequence using published sequence information.

STZ-induced diabetic mice injected with saline exhibited a significant increase in CTGF expression relative to non-diabetic mice. However, when STZ-induced diabetic mice were treated with ISIS 124212, CTGF expression was significantly decreased. The level of CTGF in diabetic mice treated with ISIS 124212 also was lower than CTGF levels in non-diabetic mice with and without oligonucleotide treatment.

Distribution of CTGF antisense oligonucleotide in the kidney (outer cortex) of control and STZ-induced mice was assessed by 2E1 staining. Kidney samples were procured, fixed in 10% neutral-buffered formalin and processed for staining with anti-oligonucleotide IgG1 antibody 2E1-B5 (Berkeley Antibody Company, Berkeley, Calif.). 2E1-B5 antibody was recognized using an isospecific anti-IgG2 horseradish peroxidase-conjugated secondary antibody (Zymed, San Francisco, Calif.) and immunostaining was developed with 3,3'-diaminobenzidene (DAKO, Carpenteria, Calif.). The results demonstrated that ISIS 124212 exhibited a similar pattern of distribution in the outer cortex of STZ-induced and non-induced mice.

Mice were further evaluated for blood glucose levels (Table 3) and body weight (Table 4). Measurements of blood glucose were taken at week 8 and week 16 and body weight was determined at week 0 and week 16.

TABLE 3

Average blood glucose levels in mg/dl (±S.D.) of STZ-induced diabetic mice treated with CTGF antisense oligonucleotide

| Diabetic Status | Treatment | Week 8 | Week 16 |
|---|---|---|---|
| Control | Saline | 127.8 ± 11.7 | 128.4 ± 18.0 |
| Control | ISIS 124212 | 108.2 ± 21.3 | 141.2 ± 19.4 |
| STZ-induced | Saline | 470.5 ± 85.6 | 516.8 ± 97.4 |
| STZ-induced | ISIS 124212 | 381.3 ± 137.5 | 474.1 ± 148.2 |

TABLE 4

Average body weight in grams (±S.D.) of STZ-induced diabetic mice treated with CTGF antisense oligonucleotide

| Diabetic Status | Treatment | Week 8 | Week 16 |
|---|---|---|---|
| Control | Saline | 24.6 ± 1.7 | 30.2 ± 1.8 |
| Control | ISIS 124212 | 29.0 ± 1.0 | 32.2 ± 1.1 |
| STZ-induced | Saline | 22.2 ± 1.1 | 25.8 ± 1.8 |
| STZ-induced | ISIS 124212 | 23.1 ± 2.6 | 26.2 ± 2.3 |

As is expected for diabetic mice, STZ-induction significantly increased blood glucose levels. Treatment with ISIS 124212 in diabetic mice resulted in slightly lower average blood glucose levels; however, the reduction was not significant. Body weight was unaffected by both STZ-induction and antisense treatment. Since CTGF is activated downstream of high glucose levels, CTGF was not expected to alter blood glucose levels or body weight in this model.

These results validate the use of CTGF antisense oligonucleotides for the reduction of CTGF mRNA expression in a mouse model of type 1 diabetes.

Example 19

Inhibition of the Development of Diabetic Nephropathy by Treatment with CTGF Antisense Oligonucleotides To evaluate whether antisense inhibition of CTGF alters the development of diabetic nephropathy, a series of experiments were performed to assess signs of the disease as well as quantitate CTGF-regulated genes and proteins involved in the development of diabetic nephropathy. For each experiment, four different treatment groups were used: non-diabetic mice injected with saline, non-diabetic mice treated with antisense oligonucleotide, STZ-induced diabetic mice injected with saline and STZ-induced diabetic mice treated with antisense oligonucleotide.

Toxic effects of compounds administered in vivo can be assessed by measuring the levels of enzymes and proteins associated with disease or injury of the liver or kidney. In accordance with the present invention, levels of albumin and urine protein were measured in STZ-induced diabetic mice and control mice treated with the compounds of the invention. Serum was analyzed by LabCorp Testing Facility (San Diego, Calif.). Levels of albumin and urine protein were normalized to urine creatinine.

TABLE 5

Average levels of albumin and urine protein in STZ-induced diabetic mice treated with CTGF antisense oligonucleotide (values normalized to urine creatinine)

| Diabetic Status | Treatment | Albumin (µg) | Urine protein (mg/24 h) |
|---|---|---|---|
| Control | Saline | 13 | 27 |
| Control | ISIS 124212 | 25 | 27 |
| STZ-induced | Saline | 42 | 58 |
| STZ-induced | ISIS 124212 | 17 | 30 |

The results demonstrate that treatment of STZ-induced diabetic mice with ISIS 124212 significantly decreases levels of albumin and urine protein relative to saline-injected diabetic mice.

Another marker of diabetic nephropathy is expansion of the mesangial matrix. STZ-induced diabetic mice and control mice treated with CTGF antisense oligonucleotide were evaluated for mesangial matrix expansion using Periodic Acid Schiff (PAS) staining according to standard procedures. Samples were evaluated by image analyses software. STZ-induced diabetic mice treated with ISIS 124212 exhibited less mesangial matrix expansion than saline control mice, indicating that CTGF antisense treatment inhibits the development of diabetic nephropathy.

CTGF has been shown to mediate TGF-beta stimulation of collagen synthesis and anchorage-independent growth of fibroblasts, suggesting that CTGF is a potential target for inhibiting fibrosis. Therefore, CTGF antisense oligonucleotides were evaluated for their ability to inhibit expression of TGF-beta in STZ-induced diabetic mice.

TGF-beta-1 target mRNA levels were determined by quantitative real-time PCR as described by other examples herein. PCR results were normalized to the ubiquitously expressed mouse 18S gene. Probes and primers to mouse TGF-beta-1 were designed to hybridize to mouse TGF-beta-1 sequence using published sequence information. For mouse TGF-beta-1, the PCR primers were:

Forward primer: AAACGGAAGCGCACTGAA (SEQ ID NO: 154)

Reverse primer: GGGACTGGCGAGCCTTAGTT (SEQ ID NO: 155)

The PCR probe was: FAM-CCATCCGTGGCCAGATC-CTGT-TAMRA (SEQ ID NO: 156), where FAM is the fluorescent dye and TAMRA is the quencher dye.

STZ-induced diabetic mice injected with saline exhibited a significant increase in TGF-beta-1 expression relative to non-diabetic mice. However, when STZ-induced diabetic mice were treated with ISIS 124212, TGF-beta-1 expression was significantly decreased, indicating that CTGF antisense treatment effectively reduces expression of downstream targets.

The effect of CTGF antisense oligonucleotide on a second downstream target, the fibronectin gene, also was determined by PCR. Fibronectin target mRNA levels were determined by quantitative real-time PCR as described by other examples herein. PCR results were normalized to the ubiquitously expressed mouse 18S gene. Probes and primers to mouse fibronectin were designed to hybridize to mouse fibronectin sequence using published sequence information. For mouse fibronectin, the PCR primers were:

Forward primer: CCGTCCATCGAGCTGACC (SEQ ID NO: 157)

Reverse primer: TGCAACGTCTTCATTCTTC (SEQ ID NO: 158)

The PCR probe was: FAM-ACCTCTTGGTGCGCTACT-CACC-TAMRA (SEQ ID NO: 159), where FAM is the fluorescent dye and TAMRA is the quencher dye.

STZ-induced diabetic mice injected with saline exhibited a significant increase in fibronectin gene expression relative to non-diabetic mice. However, when STZ-induced diabetic mice were treated with ISIS 124212, fibronectin expression was significantly decreased.

Fibronectin gene expression is activated by the transcription factor CREB. The phosphorylated form of CREB (p-CREB) represents the active form of the transcription factor. To determine whether CTGF antisense treatment of STZ-induced diabetic mice results in a reduction in p-CREB, western blots for CREB and p-CREB were performed on kidney samples as described in other examples herein. CREB and p-CREB specific antibodies (Cell Signaling Technology, Beverly, Mass.) were used at a concentration of 1:1000. STZ-induced diabetic mice exhibited significant levels of p-CREB; however, treatment with ISIS 124212 nearly eliminated p-CREB. Little to no p-CREB is detected in non-diabetic mice. Levels of CREB were similar under each condition. These results suggest that CTGF modulates fibronectin gene expression by altering the activation state of CREB.

High glucose levels are known to activate the MAPK pathway. To determine whether CTGF antisense inhibition alters activation of this pathway, western blots for p38 and phosphorylated p38 (p-p38) were performed on kidney samples. Western blots were performed as described in other examples herein using p38 and p-p38-specific antibodies (Cell Signaling Technology) at a concentration of 1:1000. Relative to non-diabetic mice, STZ-induced diabetic mice exhibit increased levels of p-p38. Treatment of diabetic mice with ISIS 124212 moderately reduced the levels of activated p-p38. Levels of p38 were similar under each condition.

Together, these results indicate that CTGF antisense inhibition is an effective means of reducing the physical signs of diabetic nephropathy as well as reducing the expression of genes involved in the development of diabetic nephropathy associated with type 1 diabetes.

Example 20

Antisense Inhibition of Connective Tissue Growth Factor in a Murine Model of Type 2 Diabetes The Animal Models of Diabetic Complications Consortium (AMDCC) has developed protocols for the induction of diabetes in a number of animal models. The genetic C57BLKS/J Lep$^{db}$/Lep$^{db}$ model has been approved by the AMDCC as an appropriate model system for studies of diabetic nephropathy associated with type 2 diabetes.

Leptin is a hormone produced by fat that regulates appetite. Deficiencies in this hormone in both humans and non-human animals lead to obesity. Lep$^{db}$/Lep$^{db}$ mice have a mutation in the leptin receptor gene which results in obesity and hyperglycemia. As such, these mice are a useful model for the investigation of obesity and diabetes and treatments designed to treat these conditions. In accordance with the present invention, oligomeric compounds of the present invention were tested in the Lep$^{db}$/Lep$^{db}$ model of type 2 diabetes.

Full phosphorothioate compound ISIS 124212 (SEQ ID NO: 39) and mixed backbone compound 334157 (SEQ ID NO: 160) were tested for their capacity to inhibit CTGF expression in vivo. Three month old C57BLKS/J Lep$^{db}$/Lep$^{db}$ and age-matched control C57BLKS/J mice were treated twice a week for six weeks with control oligonucleotide ISIS 141923 (SEQ ID NO: 161), or CTGF antisense oligonucleotides ISIS 124212 or ISIS 334157. Oligonucleotides were delivered subcutaneously at a dose of 10 mg/kg or 25 mg/kg. Saline-injected animals served as controls. Blood and urine chemistries were analyzed prior to treatment, at three weeks, and post-treatment. After the treatment period, mice are sacrificed and CTGF mRNA levels were evaluated in the kidney. RNA isolation and target mRNA expression level quantitation by quantitative PCR are performed as described in other examples herein. For mouse CTGF, the PCR primers were:

Forward primer: GCTCAGGGTAAGGTCCGATTC (SEQ ID NO: 162)

Reverse primer: GCCCCCCACCCCAAA (SEQ ID NO: 163)

The PCR probe was: FAM-TCATAATCAAAGAAGCAG-CAAGCACTTCC-TAMRA (SEQ ID NO: 164), where FAM is the fluorescent dye and TAMRA is the quencher dye.

posed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. ISIS 124212 and ISIS 141923 have phosphorothioate (P=S) internucleoside (backbone) linkages throughout the oligonucleotide. ISIS 334517 has a mixed backbone with phosphorothioate linkages in the central gap region and phosphodiester linkages in the wings. All cytidine residues in each oligonucleotide are 5-methylcytidines. Treatment with ISIS 334157 resulted in a significant decrease in CTGF expression at a dose of 25 mg/kg. ISIS 124212 also inhibited expression CTGF at the same dose.

Prior to antisense oligonucleotide treatment, expression of CTGF in Lep$^{db}$/Lep$^{db}$ kidney was assessed in 4.5 month old mice. CTGF was found to be expressed in the proximal tubular epithelial cells and in the glomeruli.

To assess distribution of CTGF antisense oligonucleotides in Lep$^{db}$/Lep$^{db}$ kidney, 2E1 staining was performed as described in other examples herein. The results demonstrated that ISIS 124212 and ISIS 334157 exhibit a similar pattern of distribution in the inner and outer cortex.

To evaluate whether antisense inhibition of CTGF alters the development of diabetic nephropathy, levels of collagen 1A and collagen IV ($\alpha$2) were determined. Collagen 1A and collagen IV target mRNA levels were determined by quantitative real-time PCR as described by other examples herein.

Probes and primers to mouse collagen 1A and collagen IV were designed to hybridize to mouse collagen 1A and collagen IV sequences using published sequence information.

For mouse collagen 1A, the PCR primers were:

Forward primer: TGGATTCCCGTTCGAGTACG (SEQ ID NO: 165)

Reverse primer: TCAGCTGGATAGCGACATCG (SEQ ID NO: 166)

The PCR probe was: FAM-AAGCGAGGGCTCCGAC-CCGA-TAMRA (SEQ ID NO: 167)

FAM is the fluorescent dye and TAMRA is the quencher dye.

For mouse collagen IV, the PCR primers were:

Forward primer: AGACCAACAAGCAAGTGAGTGC (SEQ ID NO: 168)

Reverse primer: CTAGCATGTGAGCCACATTCATCC (SEQ ID NO: 169)

The PCR probe was: FAM-CTGCTGAGGGCACGCT-GAGCT-TAMRA (SEQ ID NO: 170)

FAM is the fluorescent dye and TAMRA is the quencher dye.

TABLE 6

Antisense inhibition of CTGF mRNA in Lep$^{db}$/Lep$^{db}$ kidney (shown as percent of saline-injected control mice)

| Oligonucleotide | Percent expression of CTGF mRNA after treatment with oligonucleotide at the concentrations shown: | | |
|---|---|---|---|
| | Saline | 10 mg/kg | 25 mg/kg |
| 141923 | 100 | — | 82 |
| 124212 | 100 | 110 | 71 |
| 334157 | 100 | 83 | 53 |

ISIS 124212, ISIS 334517 and ISIS 141923 are chimeric oligonucleotides ("gapmers") 20 nucleotides in length, com-

TABLE 7

Inhibition of collagen 1A mRNA expression in Lep$^{db}$/Lep$^{db}$ mice treated with CTGF antisense oligonucleotide (shown as percent of saline-injected control mice)

| Oligonucleotide | Percent expression of collagen 1A mRNA after treatment with CTGF antisense oligonucleotide at the concentrations shown: | | |
|---|---|---|---|
| | Saline | 10 mg/kg | 25 mg/kg |
| 141923 | 100 | — | 145 |
| 124212 | 100 | 60 | 65 |
| 334157 | 100 | 78 | 75 |

TABLE 8

Inhibition of collagen IV mRNA expression in Lep$^{db}$/Lep$^{db}$ mice treated with CTGF antisense oligonucleotide (shown as percent of saline-injected control mice)

| Oligonucleotide | Percent expression of collagen IV mRNA after treatment with CTGF antisense oligonucleotide at the concentrations shown: | | |
|---|---|---|---|
| | Saline | 10 mg/kg | 25 mg/kg |
| 141923 | 100 | — | 72 |
| 124212 | 100 | 50 | 40 |
| 334157 | 100 | 37 | 24 |

Treatment with either ISIS 124212 or ISIS 334157 led to a significant reduction in mRNA expression of both collagen 1A and collagen IV in Lep$^{db}$/Lep$^{db}$ mice, relative to both saline-injected control mice and mice treated with control oligonucleotide. These results indicate that treatment with CTGF antisense oligonucleotides inhibits development of nephropathy associated with type 2 diabetes.

Toxic effects of compounds administered in vivo can be assessed by measuring the levels of enzymes and proteins associated with disease or injury of the liver or kidney. Elevations in the levels of the serum transaminases aspartate aminotransferase (AST) and alanine aminotransferase (ALT) are often indicators of liver disease or injury. To assess the physiological effects resulting from inhibition of target mRNA, the Lep$^{db}$/Lep$^{db}$ mice were further evaluated at the end of the treatment period for AST and ALT. Serum was analyzed by LabCorp Testing Facility (San Diego, Calif.). The levels of AST and ALT were within normal ranges and were not significantly changed relative to saline-treated animals, demonstrating that the mixed backbone and full phosphorothioate antisense compounds of the invention do not significantly affect hepatic function.

These results illustrate that both full phosphorothioate backbone and mixed backbone compounds inhibit expression of CTGF in vivo without toxicity. In addition, the compounds of the invention inhibit the development of diabetic nephropathy in diabetic animals.

What is claimed is:

1. An antisense oligonucleotide 20 nucleobases in length targeted to nucleotides 1707 through 1726 of a nucleic acid molecule encoding connective tissue growth factor (SEQ ID NO: 18), wherein said antisense oligonucleotide is 100% complementary to said nucleic acid molecule encoding connective tissue growth factor.

2. An antisense oligonucleotide targeted to a nucleic acid molecule encoding connective tissue growth factor (SEQ ID NO: 18), wherein said antisense oligonucleotide consists of the sequence of SEQ ID NO: 39, 40, 59 or 97.

3. The compound of claim 1 wherein the antisense oligonucleotide comprises at least one modified internucleoside linkage.

4. The compound of claim 3 wherein the modified internucleoside linkage is a phosphorothioate linkage.

5. The compound of claim 1 wherein the antisense oligonucleotide comprises at least one modified sugar moiety.

6. The compound of claim 5 wherein the modified sugar moiety is a 2'-O-methoxyethyl sugar moiety.

7. The compound of claim 1 wherein the antisense oligonucleotide comprises at least one modified nucleobase.

8. The compound of claim 1 wherein the modified nucleobase is a 5-methylcytosine.

9. The compound of claim 1 wherein the antisense oligonucleotide is a chimeric oligonucleotide.

10. The compound of claim 1, wherein said antisense oligonucleotide comprises a first region consisting of at least 5 contiguous 2'-deoxy nucleosides flanked by second and third regions, each of said second and third regions independently consisting of at least one 2'-O-methoxyethyl nucleoside.

11. The compound of claim 10 wherein the internucleoside linkages are phosphorothioate throughout.

12. The compound of claim 10 wherein the internucleoside linkages of the first region are phosphorothioate linkages and the internucleoside linkages of the second and third regions are phosphodiester linkages.

13. A composition comprising the compound of claim 1 and a pharmaceutically acceptable carrier or diluent.

14. The composition of claim 13 further comprising a colloidal dispersion system.

15. The composition of claim 13 wherein the compound is an antisense oligonucleotide.

16. An antisense oligonucleotide 20 nucleobases in length targeted to a region comprising nucleotides 1707 through 1726 of a nucleic acid molecule encoding connective tissue growth factor (SEQ ID NO: 18), wherein said antisense oligonucleotide specifically hybridizes with said nucleic acid molecule encoding connective tissue growth factor and inhibits the expression of connective tissue growth factor.

17. An antisense oligonucleotide targeted to a nucleic acid molecule encoding connective tissue growth factor (SEQ ID NO: 18), wherein said antisense oligonucleotide consists of the sequence of SEQ ID NO: 39.

18. An antisense oligonucleotide targeted to a nucleic acid molecule encoding connective tissue growth factor (SEQ ID NO: 18), wherein said antisense oligonucleotide consists of the sequence of SEQ ID NO: 40.

19. An antisense oligonucleotide 20 nucleobases in length targeted to a region comprising nucleotides 1712 through 1731 of a nucleic acid molecule encoding connective tissue growth factor (SEQ ID NO: 18), wherein said compound is 100% complementary to said nucleic acid molecule encoding connective tissue growth factor.

20. An antisense oligonucleotide targeted to a nucleic acid molecule encoding connective tissue growth factor (SEQ ID NO: 18), wherein said antisense oligonucleotide consists of the sequence of SEQ ID NO: 59.

21. An antisense oligonucleotide 20 nucleobases in length targeted to a region comprising nucleotides 1711 through 1730 of a nucleic acid molecule encoding connective tissue growth factor (SEQ ID NO: 18), wherein said compound is 100% complementary to said nucleic acid molecule encoding connective tissue growth factor.

22. An antisense oligonucleotide targeted to a nucleic acid molecule encoding connective tissue growth factor (SEQ ID NO: 18), wherein said antisense oligonucleotide consists of the sequence of SEQ ID NO: 97.

23. An antisense oligonucleotide 20 nucleobases in length targeted to a region comprising nucleotides 1697 through 1716 of a nucleic acid molecule encoding connective tissue growth factor (SEQ ID NO: 18), wherein said compound is 100% complementary to said nucleic acid molecule encoding connective tissue growth factor.

* * * * *

SEQUENCE LISTING

```
<160> NUMBER OF SEQ ID NOS: 176

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                        20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                        20

<210> SEQ ID NO 3
<211> LENGTH: 2075
<212> TYPE: DNA
<213> ORGANISM: Homo sapiens
<220> FEATURE:
<221> NAME/KEY: CDS
<222> LOCATION: (130)..(1179)

<400> SEQUENCE: 3
cccggccgac agccccgaga cgacagcccg gcgcgtcccg gtccccacct ccgaccaccg    60
ccagcgctcc aggccccgcg ctccccgctc gccgccaccg cgccctccgc tccgcccgca   120 gtgccaacc atg acc gcc gcc agt atg ggc ccc gtc cgc gtc gcc ttc gtg   171
           Met Thr Ala Ala Ser Met Gly Pro Val Arg Val Ala Phe Val
             1               5                  10 gtc ctc ctc gcc ctc tgc agc cgg ccg gcc gtc ggc cag aac tgc agc     219
Val Leu Leu Ala Leu Cys Ser Arg Pro Ala Val Gly Gln Asn Cys Ser
 15                  20                  25                  30
```

```
ggg ccg tgc cgg tgc ccg gac gag ccg gcg ccg cgc tgc ccg gcg ggc      267
Gly Pro Cys Arg Cys Pro Asp Glu Pro Ala Pro Arg Cys Pro Ala Gly
             35                  40                  45 gtg agc ctc gtg ctg gac ggc tgc ggc tgc tgc cgc gtc tgc gcc aag      315
Val Ser Leu Val Leu Asp Gly Cys Gly Cys Cys Arg Val Cys Ala Lys
         50                  55                  60 cag ctg ggc gag ctg tgc acc gag cgc gac ccc tgc gac ccg cac aag      363
Gln Leu Gly Glu Leu Cys Thr Glu Arg Asp Pro Cys Asp Pro His Lys
             65                  70                  75 ggc ctc ttc tgt gac ttc ggc tcc ccg gcc aac cgc aag atc ggc gtg      411
Gly Leu Phe Cys Asp Phe Gly Ser Pro Ala Asn Arg Lys Ile Gly Val
         80                  85                  90 tgc acc gcc aaa gat ggt gct ccc tgc atc ttc ggt ggt acg gtg tac      459
Cys Thr Ala Lys Asp Gly Ala Pro Cys Ile Phe Gly Gly Thr Val Tyr
95                  100                 105                 110 cgc agc gga gag tcc ttc cag agc agc tgc aag tac cag tgc acg tgc      507
Arg Ser Gly Glu Ser Phe Gln Ser Ser Cys Lys Tyr Gln Cys Thr Cys
                 115                 120                 125 ctg gac ggg gcg gtg ggc tgc atg ccc ctg tgc agc atg gac gtt cgt      555
Leu Asp Gly Ala Val Gly Cys Met Pro Leu Cys Ser Met Asp Val Arg
             130                 135                 140 ctg ccc agc cct gac tgc ccc ttc ccg agg agg gtc aag ctg ccc ggg      603
Leu Pro Ser Pro Asp Cys Pro Phe Pro Arg Arg Val Lys Leu Pro Gly
         145                 150                 155 aaa tgc tgc gag gag tgg gtg tgt gac gag ccc aag gac caa acc gtg      651
Lys Cys Cys Glu Glu Trp Val Cys Asp Glu Pro Lys Asp Gln Thr Val
         160                 165                 170 gtt ggg cct gcc ctc gcg gct tac cga ctg gaa gac acg ttt ggc cca      699
Val Gly Pro Ala Leu Ala Ala Tyr Arg Leu Glu Asp Thr Phe Gly Pro
175                 180                 185                 190 gac cca act atg att aga gcc aac tgc ctg gtc cag acc aca gag tgg      747
Asp Pro Thr Met Ile Arg Ala Asn Cys Leu Val Gln Thr Thr Glu Trp
                 195                 200                 205 agc gcc tgt tcc aag acc tgt ggg atg ggc atc tcc acc cgg gtt acc      795
Ser Ala Cys Ser Lys Thr Cys Gly Met Gly Ile Ser Thr Arg Val Thr
             210                 215                 220 aat gac aac gcc tcc tgc agg cta gag aag cag agc cgc ctg tgc atg      843
Asn Asp Asn Ala Ser Cys Arg Leu Glu Lys Gln Ser Arg Leu Cys Met
         225                 230                 235 gtc agg cct tgc gaa gct gac ctg gaa gag aac att aag aag ggc aaa      891
Val Arg Pro Cys Glu Ala Asp Leu Glu Glu Asn Ile Lys Lys Gly Lys
         240                 245                 250 aag tgc atc cgt act ccc aaa atc tcc aag cct atc aag ttt gag ctt      939
Lys Cys Ile Arg Thr Pro Lys Ile Ser Lys Pro Ile Lys Phe Glu Leu
255                 260                 265                 270 tct ggc tgc acc agc atg aag aca tac cga gct aaa ttc tgt gga gta      987
Ser Gly Cys Thr Ser Met Lys Thr Tyr Arg Ala Lys Phe Cys Gly Val
                 275                 280                 285 tgt acc gac ggc cga tgc tgc acc ccc cac aga acc acc acc ctg ccg     1035
Cys Thr Asp Gly Arg Cys Cys Thr Pro His Arg Thr Thr Thr Leu Pro
             290                 295                 300 gtg gag ttc aag tgc cct gac ggc gag gtc atg aag aag aac atg atg     1083
Val Glu Phe Lys Cys Pro Asp Gly Glu Val Met Lys Lys Asn Met Met
         305                 310                 315 ttc atc aag acc tgt gcc tgc cat tac aac tgt ccc gga gac aat gac     1131
Phe Ile Lys Thr Cys Ala Cys His Tyr Asn Cys Pro Gly Asp Asn Asp
         320                 325                 330 atc ttt gaa tcg ctg tac tac agg aag atg tac gga gac atg gca tga     1179
Ile Phe Glu Ser Leu Tyr Tyr Arg Lys Met Tyr Gly Asp Met Ala
```

-continued

```
                335         340         345
agccagagag tgagagacat taactcatta gactggaact tgaactgatt cacatctcat    1239
ttttccgtaa aaatgatttc agtagcacaa gttatttaaa tctgttttto taactggggg    1299 aaaagattcc cacccaattc aaaacattgt gccatgtcaa acaaatagtc tatcttcccc    1359
agacactggt ttgaagaatg ttaagacttg acagtggaac tacattagta cacagcacca    1419
gaatgtatat taaggtgtgg ctttaggagc agtgggaggg taccggcccg gttagtatca    1479
tcagatcgac tcttatacga gtaatatgcc tgctatttga agtgtaattg agaaggaaaa    1539
ttttagcgtg ctcactgacc tgcctgtagc cccagtgaca gctaggatgt gcattctcca    1599
gccatcaaga gactgagtca agttgttcct taagtcagaa cagcagactc agctctgaca    1659
ttctgattcg aatgacactg ttcaggaatc ggaatcctgt cgattagact ggacagcttg    1719
tggcaagtga atttgcctgt aacaagccag attttttaaa atttatattg taaatattgt    1779
gtgtgtgtgt gtgtgtgtat atatatatat atatgtacag ttatctaagt taatttaaag    1839
ttgtttgtgc cttttatttt ttgttttttaa tgctttgata tttcaatgtt agcctcaatt    1899
tctgaacacc ataggtagaa tgtaaagctt gtctgatcgt tcaaagcatg aaatggatac    1959
ttatatggaa attctgctca gatagaatga cagtccgtca aaacagattg tttgcaaagg    2019
ggaggcatca gtgtcttggc aggctgattt ctaggtagga aatgtggtag ctcacg        2075
```

<210> SEQ ID NO 4
<211> LENGTH: 349
<212> TYPE: PRT
<213> ORGANISM: Homo sapiens

<400> SEQUENCE: 4

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205
```

-continued

```
Cys Ser Lys Thr Cys Gly Met Gly Ile Ser Thr Arg Val Thr Asn Asp
            210                 215                 220
Asn Ala Ser Cys Arg Leu Glu Lys Gln Ser Arg Leu Cys Met Val Arg
225                 230                 235                 240
Pro Cys Glu Ala Asp Leu Glu Glu Asn Ile Lys Lys Gly Lys Lys Cys
                245                 250                 255
Ile Arg Thr Pro Lys Ile Ser Lys Pro Ile Lys Phe Glu Leu Ser Gly
                260                 265                 270
Cys Thr Ser Met Lys Thr Tyr Arg Ala Lys Phe Cys Gly Val Cys Thr
            275                 280                 285
Asp Gly Arg Cys Cys Thr Pro His Arg Thr Thr Thr Leu Pro Val Glu
    290                 295                 300
Phe Lys Cys Pro Asp Gly Glu Val Met Lys Lys Asn Met Met Phe Ile
305                 310                 315                 320
Lys Thr Cys Ala Cys His Tyr Asn Cys Pro Gly Asp Asn Asp Ile Phe
                325                 330                 335
Glu Ser Leu Tyr Tyr Arg Lys Met Tyr Gly Asp Met Ala
            340                 345

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
acaagggcct cttctgtgac tt                                          22

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
ggtacaccgt accaccgaag at                                          22

<210> SEQ ID NO 7
<211> LENGTH: 23
<212> TYPE: DNA
<213> ORGANISM: Artificial Sequence
<220> FEATURE:
<223> OTHER INFORMATION: PCR Probe

<400> SEQUENCE: 7
tgtgcaccgc caaagatggt gct                                         23

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                              19

<210> SEQ ID NO 9
<211> LENGTH: 20
<212> TYPE: DNA
```

<213> ORGANISM: Artificial Sequence
<220> FEATURE:
<223> OTHER INFORMATION: PCR Primer

<400> SEQUENCE: 9
gaagatggtg atgggatttc                                          20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                          20

<210> SEQ ID NO 11
<211> LENGTH: 2334
<212> TYPE: DNA
<213> ORGANISM: Mus musculus
<220> FEATURE:
<221> NAME/KEY: CDS
<222> LOCATION: (206)..(1252)

<400> SEQUENCE: 11

```
gaagactcag ccagatccac tccagctccg accccaggag accgacctcc tccagacggc          60
agcagcccca gcccagccga caaccccaga cgccaccgcc tggagcgtcc agacaccaac         120
ctccgcccct gtccgaatcc aggctccggc cgcgcctctc gtcgcctctg caccctgctg         180
tgcatcctcc taccgcgtcc cgatc atg ctc gcc tcc gtc gca ggt ccc atc          232
                            Met Leu Ala Ser Val Ala Gly Pro Ile
                              1               5 agc ctc gcc ttg gtg ctc ctc gcc ctc tgc acc cgg cct gct acg ggc          280
Ser Leu Ala Leu Val Leu Leu Ala Leu Cys Thr Arg Pro Ala Thr Gly
 10                  15                  20                  25 cag gac tgc agc gcg caa tgt cag tgc gca gcc gaa gca gcg ccg cac          328
Gln Asp Cys Ser Ala Gln Cys Gln Cys Ala Ala Glu Ala Ala Pro His
                 30                  35                  40 tgc ccc gcc ggc gtg agc ctg gtg ctg gac ggc tgc ggc tgc tgc cgc          376
Cys Pro Ala Gly Val Ser Leu Val Leu Asp Gly Cys Gly Cys Cys Arg
             45                  50                  55 gtc tgc gcc aag cag ctg gga gaa ctg tgt acg gag cgt gac ccc tgc          424
Val Cys Ala Lys Gln Leu Gly Glu Leu Cys Thr Glu Arg Asp Pro Cys
         60                  65                  70 gac cca cac aag ggc ctc ttc tgc gat ttc ggc tcc ccc gcc aac cgc          472
Asp Pro His Lys Gly Leu Phe Cys Asp Phe Gly Ser Pro Ala Asn Arg
     75                  80                  85 aag atc gga gtg tgc act gcc aaa gat ggt gca ccc tgt gtc ttc ggt          520
Lys Ile Gly Val Cys Thr Ala Lys Asp Gly Ala Pro Cys Val Phe Gly
 90                  95                 100                 105 ggg tcg gtg tac cgc agc ggt gag tcc ttc caa agc agc tgc aaa tac          568
Gly Ser Val Tyr Arg Ser Gly Glu Ser Phe Gln Ser Ser Cys Lys Tyr
                110                 115                 120 caa tgc act tgc ctg gat ggg gcc gtg ggc tgc gtg ccc ctg tgc agc          616
Gln Cys Thr Cys Leu Asp Gly Ala Val Gly Cys Val Pro Leu Cys Ser
            125                 130                 135 atg gac gtg cgc ctg ccc agc cct gac tgc ccc ttc ccg aga agg gtc          664
Met Asp Val Arg Leu Pro Ser Pro Asp Cys Pro Phe Pro Arg Arg Val
        140                 145                 150 aag ctg cct ggg aaa tgc tgc gag gag tgg gtg tgt gac gag ccc aag          712
Lys Leu Pro Gly Lys Cys Cys Glu Glu Trp Val Cys Asp Glu Pro Lys
```

-continued

|  |  |  |  |  |  |  |  |  |  |  |  |  |  |  |  |
|---|---|---|---|---|---|---|---|---|---|---|---|---|---|---|---|
|  | 155 |  |  |  | 160 |  |  |  |  | 165 |  |  |  |  |  |
| gac | cgc | aca | gca | gtt | ggc | cct | gcc | cta | gct | gcc | tac | cga | ctg | gaa | gac | 760 |
| Asp | Arg | Thr | Ala | Val | Gly | Pro | Ala | Leu | Ala | Ala | Tyr | Arg | Leu | Glu | Asp |  |
| 170 |  |  |  | 175 |  |  |  |  | 180 |  |  |  |  | 185 |  |  |
| aca | ttt | ggc | cca | gac | cca | act | atg | atg | cga | gcc | aac | tgc | ctg | gtc | cag | 808 |
| Thr | Phe | Gly | Pro | Asp | Pro | Thr | Met | Met | Arg | Ala | Asn | Cys | Leu | Val | Gln |  |
|  |  |  |  | 190 |  |  |  |  | 195 |  |  |  |  | 200 |  |  |
| acc | aca | gag | tgg | agc | gcc | tgt | tct | aag | acc | tgt | ggg | atg | ggc | atc | tcc | 856 |
| Thr | Thr | Glu | Trp | Ser | Ala | Cys | Ser | Lys | Thr | Cys | Gly | Met | Gly | Ile | Ser |  |
|  |  |  |  | 205 |  |  |  |  | 210 |  |  |  |  | 215 |  |  |
| acc | cga | gtt | acc | aat | gac | aat | acc | ttc | tgc | aga | ctt | gag | aag | cag | agt | 904 |
| Thr | Arg | Val | Thr | Asn | Asp | Asn | Thr | Phe | Cys | Arg | Leu | Glu | Lys | Gln | Ser |  |
|  |  |  | 220 |  |  |  |  | 225 |  |  |  |  | 230 |  |  |  |
| cgc | ctc | tgc | atg | gtc | agg | ccc | tgc | gaa | gct | gac | ctg | gag | gaa | aac | att | 952 |
| Arg | Leu | Cys | Met | Val | Arg | Pro | Cys | Glu | Ala | Asp | Leu | Glu | Glu | Asn | Ile |  |
|  | 235 |  |  |  |  | 240 |  |  |  |  | 245 |  |  |  |  |  |
| aag | aag | ggc | aaa | aag | tgc | atc | cgg | aca | cct | aaa | atc | gcc | aag | cct | gtc | 1000 |
| Lys | Lys | Gly | Lys | Lys | Cys | Ile | Arg | Thr | Pro | Lys | Ile | Ala | Lys | Pro | Val |  |
| 250 |  |  |  |  | 255 |  |  |  |  | 260 |  |  |  |  | 265 |  |
| aag | ttt | gag | ctt | tct | ggc | tgc | acc | agt | gtg | aag | aca | tac | agg | gct | aag | 1048 |
| Lys | Phe | Glu | Leu | Ser | Gly | Cys | Thr | Ser | Val | Lys | Thr | Tyr | Arg | Ala | Lys |  |
|  |  |  |  | 270 |  |  |  |  | 275 |  |  |  |  | 280 |  |  |
| ttc | tgc | ggg | gtg | tgc | aca | gac | ggc | cgc | tgc | tgc | aca | ccg | cac | aga | acc | 1096 |
| Phe | Cys | Gly | Val | Cys | Thr | Asp | Gly | Arg | Cys | Cys | Thr | Pro | His | Arg | Thr |  |
|  |  |  | 285 |  |  |  |  | 290 |  |  |  |  | 295 |  |  |  |
| acc | act | ctg | cca | gtg | gag | ttc | aaa | tgc | ccc | gat | ggc | gag | atc | atg | aaa | 1144 |
| Thr | Thr | Leu | Pro | Val | Glu | Phe | Lys | Cys | Pro | Asp | Gly | Glu | Ile | Met | Lys |  |
|  |  | 300 |  |  |  |  | 305 |  |  |  |  | 310 |  |  |  |  |
| aag | aat | atg | atg | ttc | atc | aag | acc | tgt | gcc | tgc | cat | tac | aac | tgt | cct | 1192 |
| Lys | Asn | Met | Met | Phe | Ile | Lys | Thr | Cys | Ala | Cys | His | Tyr | Asn | Cys | Pro |  |
|  | 315 |  |  |  |  | 320 |  |  |  |  | 325 |  |  |  |  |  |
| ggg | gac | aat | gac | atc | ttt | gag | tcc | ctg | tac | tac | agg | aag | atg | tac | gga | 1240 |
| Gly | Asp | Asn | Asp | Ile | Phe | Glu | Ser | Leu | Tyr | Tyr | Arg | Lys | Met | Tyr | Gly |  |
| 330 |  |  |  |  | 335 |  |  |  |  | 340 |  |  |  |  | 345 |  |
| gac | atg | gcg | taa | agccaggaag | taagggacac | gaactcatta | gactataact |  |  |  |  |  |  |  |  | 1292 |
| Asp | Met | Ala |  |  |  |  |  |  |  |  |  |  |  |  |  |  |
| tgaactgagt | tgcatctcat | tttcttctgt | aaaaacaatt | acagtagcac | attaatttaa |  |  |  |  |  |  |  |  |  |  | 1352 |
| atctgtgttt | ttaactaccg | tgggaggaac | tatcccacca | aagtgagaac | gttatgtcat |  |  |  |  |  |  |  |  |  |  | 1412 |
| ggccatacaa | gtagtctgtc | aacctcagac | actggtttcg | agacagttta | cacttgacag |  |  |  |  |  |  |  |  |  |  | 1472 |
| ttgttcatta | gcgcacagtg | ccagaacgca | cactgaggtg | agtctcctgg | aacagtggag |  |  |  |  |  |  |  |  |  |  | 1532 |
| atgccaggag | aaagaaagac | aggtactagc | tgaggttatt | ttaaaagcag | cagtgtgcct |  |  |  |  |  |  |  |  |  |  | 1592 |
| acttttttgga | gtgtaaccgg | ggagggcaat | tatagcatgc | ttgcagacag | acctgctcta |  |  |  |  |  |  |  |  |  |  | 1652 |
| gcgagagctg | agcatgtgtc | ctccactaga | tgaggctgag | tccagctgtt | ctttaagaac |  |  |  |  |  |  |  |  |  |  | 1712 |
| agcagtttca | gctctgacca | ttctgattcc | agtgacactt | gtcaggagtc | agagccttgt |  |  |  |  |  |  |  |  |  |  | 1772 |
| ctgttagact | ggacagcttg | tggcaagtaa | gtttgcctgt | aacaagccag | attttttattg |  |  |  |  |  |  |  |  |  |  | 1832 |
| atattgtaaa | tattgtggat | atatatatat | atatatttgt | acagttatct | aagttaatt |  |  |  |  |  |  |  |  |  |  | 1892 |
| aaagtcattt | gttttttgttt | taagtgcttt | tgggatttta | aactgatagc | ctcaaactcc |  |  |  |  |  |  |  |  |  |  | 1952 |
| aaacaccata | ggtaggacac | gaagcttatc | tgtgattcaa | aacaaaggag | atactgcagt |  |  |  |  |  |  |  |  |  |  | 2012 |
| gggaattgtg | acctgagtga | ctctctgtca | gaacaaatgc | tgtgcaggtg | ataaagctat |  |  |  |  |  |  |  |  |  |  | 2072 |
| gtattggaag | tcagatttct | agtaggaaat | gtggtcaaat | ccctgttggt | gaacaaatgg |  |  |  |  |  |  |  |  |  |  | 2132 |
| cctttattaa | gaaatggctg | gctcagggta | aggtccgatt | cctaccagga | agtgcttgct |  |  |  |  |  |  |  |  |  |  | 2192 |

```
gcttctttga ttatgactgg tttggggtgg ggggcagttt atttgttgag agtgtgacca    2252
aaagttacat gtttgcacct ttctagttga aaataaagta tatatatatt ttttatatga    2312
aaaaaaaaaa aaaaaaaaaa aa                                             2334
```

<210> SEQ ID NO 12
<211> LENGTH: 348
<212> TYPE: PRT
<213> ORGANISM: Mus musculus

<400> SEQUENCE: 12

```
Met Leu Ala Ser Val Ala Gly Pro Ile Ser Leu Ala Leu Val Leu Leu
1               5                   10                  15

Ala Leu Cys Thr Arg Pro Ala Thr Gly Gln Asp Cys Ser Ala Gln Cys
            20                  25                  30

Gln Cys Ala Ala Glu Ala Ala Pro His Cys Pro Ala Gly Val Ser Leu
        35                  40                  45

Val Leu Asp Gly Cys Gly Cys Cys Arg Val Cys Ala Lys Gln Leu Gly
    50                  55                  60

Glu Leu Cys Thr Glu Arg Asp Pro Cys Asp Pro His Lys Gly Leu Phe
65                  70                  75                  80

Cys Asp Phe Gly Ser Pro Ala Asn Arg Lys Ile Gly Val Cys Thr Ala
                85                  90                  95

Lys Asp Gly Ala Pro Cys Val Phe Gly Gly Ser Val Tyr Arg Ser Gly
            100                 105                 110

Glu Ser Phe Gln Ser Ser Cys Lys Tyr Gln Cys Thr Cys Leu Asp Gly
        115                 120                 125

Ala Val Gly Cys Val Pro Leu Cys Ser Met Asp Val Arg Leu Pro Ser
    130                 135                 140

Pro Asp Cys Pro Phe Pro Arg Arg Val Lys Leu Pro Gly Lys Cys Cys
145                 150                 155                 160

Glu Glu Trp Val Cys Asp Glu Pro Lys Asp Arg Thr Ala Val Gly Pro
                165                 170                 175

Ala Leu Ala Ala Tyr Arg Leu Glu Asp Thr Phe Gly Pro Asp Pro Thr
            180                 185                 190

Met Met Arg Ala Asn Cys Leu Val Gln Thr Thr Glu Trp Ser Ala Cys
        195                 200                 205

Ser Lys Thr Cys Gly Met Gly Ile Ser Thr Arg Val Thr Asn Asp Asn
    210                 215                 220

Thr Phe Cys Arg Leu Glu Lys Gln Ser Arg Leu Cys Met Val Arg Pro
225                 230                 235                 240

Cys Glu Ala Asp Leu Glu Glu Asn Ile Lys Lys Gly Lys Lys Cys Ile
                245                 250                 255

Arg Thr Pro Lys Ile Ala Lys Pro Val Lys Phe Glu Leu Ser Gly Cys
            260                 265                 270

Thr Ser Val Lys Thr Tyr Arg Ala Lys Phe Cys Gly Val Cys Thr Asp
        275                 280                 285

Gly Arg Cys Cys Thr Pro His Arg Thr Thr Thr Leu Pro Val Glu Phe
    290                 295                 300

Lys Cys Pro Asp Gly Glu Ile Met Lys Lys Asn Met Met Phe Ile Lys
305                 310                 315                 320

Thr Cys Ala Cys His Tyr Asn Cys Pro Gly Asp Asn Asp Ile Phe Glu
                325                 330                 335

Ser Leu Tyr Tyr Arg Lys Met Tyr Gly Asp Met Ala
            340                 345
```

-continued

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
gctcagggta aggtccgatt c                                        21

<210> SEQ ID NO 14
<211> LENGTH: 15
<212> TYPE: DNA
<213> ORGANISM: Artificial Sequence
<220> FEATURE:
<223> OTHER INFORMATION: PCR Primer

<400> SEQUENCE: 14 gcccccacc ccaaa                                                15

<210> SEQ ID NO 15
<211> LENGTH: 31
<212> TYPE: DNA
<213> ORGANISM: Artificial Sequence
<220> FEATURE:
<223> OTHER INFORMATION: PCR Probe

<400> SEQUENCE: 15
tcataatcaa agaagcagca agcacttcct g                             31

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
ggcaaattca acggcacagt                                          20

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
gggtctcgct cctggaagat                                          20

<210> SEQ ID NO 18
<211> LENGTH: 27
<212> TYPE: DNA
<213> ORGANISM: Artificial Sequence
<220> FEATURE:
<223> OTHER INFORMATION: PCR Probe

<400> SEQUENCE: 18
aaggccgaga atgggaagct tgtcatc                                  27

<210> SEQ ID NO 19
<211> LENGTH: 2312
<212> TYPE: DNA
<213> ORGANISM: Homo sapiens
<220> FEATURE:

<221> NAME/KEY: CDS
<222> LOCATION: (146)..(1195)

<400> SEQUENCE: 19

```
tccagtgacg gagccgcccg gccgacagcc ccgagacgac agcccggcgc gtcccggtcc      60
ccacctccga ccaccgccag cgctccaggc cccgcgctcc ccgctcgccg ccaccgcgcc     120
ctccgctccg cccgcagtgc caacc atg acc gcc gcc agt atg ggc ccc gtc      172
                              Met Thr Ala Ala Ser Met Gly Pro Val
                                1               5 cgc gtc gcc ttc gtg gtc ctc ctc gcc ctc tgc agc cgg ccg gcc gtc      220
Arg Val Ala Phe Val Val Leu Leu Ala Leu Cys Ser Arg Pro Ala Val
 10              15                  20                  25 ggc cag aac tgc agc ggg ccg tgc cgg tgc ccg gac gag ccg gcg ccg      268
Gly Gln Asn Cys Ser Gly Pro Cys Arg Cys Pro Asp Glu Pro Ala Pro
             30                  35                  40 cgc tgc ccg gcg ggc gtg agc ctc gtg ctg gac ggc tgc ggc tgc tgc      316
Arg Cys Pro Ala Gly Val Ser Leu Val Leu Asp Gly Cys Gly Cys Cys
         45                  50                  55 cgc gtc tgc gcc aag cag ctg ggc gag ctg tgc acc gag cgc gac ccc      364
Arg Val Cys Ala Lys Gln Leu Gly Glu Leu Cys Thr Glu Arg Asp Pro
     60                  65                  70 tgc gac ccg cac aag ggc ctc ttc tgt gac ttc ggc tcc ccg gcc aac      412
Cys Asp Pro His Lys Gly Leu Phe Cys Asp Phe Gly Ser Pro Ala Asn
 75                  80                  85 cgc aag atc ggc gtg tgc acc gcc aaa gat ggt gct ccc tgc atc ttc      460
Arg Lys Ile Gly Val Cys Thr Ala Lys Asp Gly Ala Pro Cys Ile Phe
 90                  95                 100                 105 ggt ggt acg gtg tac cgc agc gga gag tcc ttc cag agc agc tgc aag      508
Gly Gly Thr Val Tyr Arg Ser Gly Glu Ser Phe Gln Ser Ser Cys Lys
                110                 115                 120 tac cag tgc acg tgc ctg gac ggg gcg gtg ggc tgc atg ccc ctg tgc      556
Tyr Gln Cys Thr Cys Leu Asp Gly Ala Val Gly Cys Met Pro Leu Cys
            125                 130                 135 agc atg gac gtt cgt ctg ccc agc cct gac tgc ccc ttc ccg agg agg      604
Ser Met Asp Val Arg Leu Pro Ser Pro Asp Cys Pro Phe Pro Arg Arg
        140                 145                 150 gtc aag ctg ccc ggg aaa tgc tgc gag gag tgg gtg tgt gac gag ccc      652
Val Lys Leu Pro Gly Lys Cys Cys Glu Glu Trp Val Cys Asp Glu Pro
    155                 160                 165 aag gac caa acc gtg gtt ggg cct gcc ctc gcg gct tac cga ctg gaa      700
Lys Asp Gln Thr Val Val Gly Pro Ala Leu Ala Ala Tyr Arg Leu Glu
170                 175                 180                 185 gac acg ttt ggc cca gac cca act atg att aga gcc aac tgc ctg gtc      748
Asp Thr Phe Gly Pro Asp Pro Thr Met Ile Arg Ala Asn Cys Leu Val
                190                 195                 200 cag acc aca gag tgg agc gcc tgt tcc aag acc tgt ggg atg ggc atc      796
Gln Thr Thr Glu Trp Ser Ala Cys Ser Lys Thr Cys Gly Met Gly Ile
            205                 210                 215 tcc acc cgg gtt acc aat gac aac gcc tcc tgc agg cta gag aag cag      844
Ser Thr Arg Val Thr Asn Asp Asn Ala Ser Cys Arg Leu Glu Lys Gln
        220                 225                 230 agc cgc ctg tgc atg gtc agg cct tgc gaa gct gac ctg gaa gag aac      892
Ser Arg Leu Cys Met Val Arg Pro Cys Glu Ala Asp Leu Glu Glu Asn
    235                 240                 245 att aag aag ggc aaa aag tgc atc cgt act ccc aaa atc tcc aag cct      940
Ile Lys Lys Gly Lys Lys Cys Ile Arg Thr Pro Lys Ile Ser Lys Pro
250                 255                 260                 265 atc aag ttt gag ctt tct ggc tgc acc agc atg aag aca tac cga gct      988
Ile Lys Phe Glu Leu Ser Gly Cys Thr Ser Met Lys Thr Tyr Arg Ala
```

-continued

```
                      270                 275                 280
aaa ttc tgt gga gta tgt acc gac ggc cga tgc tgc acc ccc cac aga    1036
Lys Phe Cys Gly Val Cys Thr Asp Gly Arg Cys Cys Thr Pro His Arg
            285                 290                 295 acc acc acc ctg ccg gtg gag ttc aag tgc cct gac ggc gag gtc atg    1084
Thr Thr Thr Leu Pro Val Glu Phe Lys Cys Pro Asp Gly Glu Val Met
        300                 305                 310 aag aag aac atg atg ttc atc aag acc tgt gcc tgc cat tac aac tgt    1132
Lys Lys Asn Met Met Phe Ile Lys Thr Cys Ala Cys His Tyr Asn Cys
    315                 320                 325 ccc gga gac aat gac atc ttt gaa tcg ctg tac tac agg aag atg tac    1180
Pro Gly Asp Asn Asp Ile Phe Glu Ser Leu Tyr Tyr Arg Lys Met Tyr
330                 335                 340                 345 gga gac atg gca tga agccagagag tgagagacat taactcatta gactggaact    1235
Gly Asp Met Ala tgaactgatt cacatctcat ttttccgtaa aaatgattte agtagcacaa gttatttaaa    1295
tctgtttttc taactggggg aaaagattcc cacccaattc aaaacattgt gccatgtcaa    1355
acaaatagtc tatcttcccc agacactggt ttgaagaatg ttaagacttg acagtggaac    1415
tacattagta cacagcacca gaatgtatat taaggtgtgg ctttaggagc agtgggaggg    1475
taccagcaga aaggttagta tcatcagata gctcttatac gagtaatatg cctgctattt    1535
gaagtgtaat tgagaaggaa aattttagcg tgctcactga cctgcctgta gccccagtga    1595
cagctaggat gtgcattctc cagccatcaa gagactgagt caagttgttc cttaagtcag    1655
aacagcagac tcagctctga cattctgatt cgaatgacac tgttcaggaa tcggaatcct    1715
gtcgattaga ctggacagct tgtggcaagt gaattcctg taacaagcca gattttttaa    1775
aatttatatt gtaaatattg tgtgtgtgtg tgtgtgtgta tatatatata tatatgtaca    1835
gttatctaag ttaatttaaa gttgtttgtg ccttttatt tttgttttta atgctttgat    1895
atttcaatgt tagcctcaat ttctgaacac cataggtaga atgtaaagct tgtctgatcg    1955
ttcaaagcat gaaatggata cttatatgga aattctctca gatagaatga cagtccgtca    2015
aaacagattg tttgcaaagg ggaggcatca gtgtccttgg caggctgatt tctaggtagg    2075
aaatgtggta gctcacgctc acttttaatg aacaaatggc ctttattaaa aactgagtga    2135
ctctatatag ctgatcagtt ttttcacctg gaagcatttg tttctacttt gatatgactg    2195
tttttcggac agtttatttg ttgagagtgt gaccaaaagt tacatgtttg cacctttcta    2255
gttgaaaata agtatatttt tttctaaaaa aaaaaaaaa cgacagcaac ggaattc       2312
```

<210> SEQ ID NO 20
<211> LENGTH: 349
<212> TYPE: PRT
<213> ORGANISM: Homo sapiens

<400> SEQUENCE: 20

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80
```

```
Phe Cys Asp Phe Gly Ser Pro Ala Asn Arg Lys Ile Gly Val Cys Thr
                85                  90                  95
Ala Lys Asp Gly Ala Pro Cys Ile Phe Gly Thr Val Tyr Arg Ser
            100                 105                 110
Gly Glu Ser Phe Gln Ser Ser Cys Lys Tyr Gln Cys Thr Cys Leu Asp
        115                 120                 125
Gly Ala Val Gly Cys Met Pro Leu Cys Ser Met Asp Val Arg Leu Pro
    130                 135                 140
Ser Pro Asp Cys Pro Phe Pro Arg Arg Val Lys Leu Pro Gly Lys Cys
145                 150                 155                 160
Cys Glu Glu Trp Val Cys Asp Glu Pro Lys Asp Gln Thr Val Val Gly
                165                 170                 175
Pro Ala Leu Ala Ala Tyr Arg Leu Glu Asp Thr Phe Gly Pro Asp Pro
            180                 185                 190
Thr Met Ile Arg Ala Asn Cys Leu Val Gln Thr Thr Glu Trp Ser Ala
        195                 200                 205
Cys Ser Lys Thr Cys Gly Met Gly Ile Ser Thr Arg Val Thr Asn Asp
    210                 215                 220
Asn Ala Ser Cys Arg Leu Glu Lys Gln Ser Arg Leu Cys Met Val Arg
225                 230                 235                 240
Pro Cys Glu Ala Asp Leu Glu Glu Asn Ile Lys Lys Gly Lys Lys Cys
                245                 250                 255
Ile Arg Thr Pro Lys Ile Ser Lys Pro Ile Lys Phe Glu Leu Ser Gly
            260                 265                 270
Cys Thr Ser Met Lys Thr Tyr Arg Ala Lys Phe Cys Gly Val Cys Thr
        275                 280                 285
Asp Gly Arg Cys Cys Thr Pro His Arg Thr Thr Thr Leu Pro Val Glu
    290                 295                 300
Phe Lys Cys Pro Asp Gly Glu Val Met Lys Lys Asn Met Met Phe Ile
305                 310                 315                 320
Lys Thr Cys Ala Cys His Tyr Asn Cys Pro Gly Asp Asn Asp Ile Phe
                325                 330                 335
Glu Ser Leu Tyr Tyr Arg Lys Met Tyr Gly Asp Met Ala
            340                 345

<210> SEQ ID NO 21
<211> LENGTH: 2078
<212> TYPE: DNA
<213> ORGANISM: Homo sapiens
<220> FEATURE:
<221> NAME/KEY: CDS
<222> LOCATION: (131)..(1180)

<400> SEQUENCE: 21
cccggccgac agccccgaga cgacagcccg gcgcgtcccg gtccccacct ccgaccaccg    60
ccagcgctcc aggccccgcc gctccccgct cgccgccacc gcgccctccg ctccgcccgc   120
agtgccaacc atg acc gcc gcc agt atg ggc ccc gtc cgc gtc gcc ttc      169
            Met Thr Ala Ala Ser Met Gly Pro Val Arg Val Ala Phe
            1               5                   10 gtg gtc ctc ctc gcc ctc tgc agc cgg ccg gcc gtc ggc cag aac tgc     217
Val Val Leu Leu Ala Leu Cys Ser Arg Pro Ala Val Gly Gln Asn Cys
    15                  20                  25 agc ggg ccg tgc cgg tgc ccg gac gag ccg gcg ccg cgc tgc ccg gcg     265
Ser Gly Pro Cys Arg Cys Pro Asp Glu Pro Ala Pro Arg Cys Pro Ala
30                  35                  40                  45
```

| | | | | | | | | | | | | | | | | |
|---|---|---|---|---|---|---|---|---|---|---|---|---|---|---|---|---|
| ggc | gtg | agc | ctc | gtg | ctg | gac | ggc | tgc | ggc | tgc | tgc | cgc | gtc | tgc | gcc | 313 |
| Gly | Val | Ser | Leu 50 | Val | Leu | Asp | Gly | Cys 55 | Gly | Cys | Cys | Arg | Val 60 | Cys | Ala | |
| aag | cag | ctg | ggc | gag | ctg | tgc | acc | gag | cgc | gac | cca | tgc | gac | ccg | cac | 361 |
| Lys | Gln | Leu | Gly 65 | Glu | Leu | Cys | Thr 70 | Glu | Arg | Asp | Pro | Cys 75 | Asp | Pro | His | |
| aag | ggc | cta | ttc | tgt | cac | ttc | ggc | tcc | ccg | gcc | aac | cgc | aag | atc | ggc | 409 |
| Lys | Gly | Leu | Phe 80 | Cys | His | Phe | Gly 85 | Ser | Pro | Ala | Asn | Arg 90 | Lys | Ile | Gly | |
| gtg | tgc | acc | gcc | aaa | gat | ggt | gct | ccc | tgc | atc | ttc | ggt | ggt | acg | gtg | 457 |
| Val | Cys | Thr | Ala 95 | Lys | Asp | Gly | Ala 100 | Pro | Cys | Ile | Phe | Gly 105 | Gly | Thr | Val | |
| tac | cgc | agc | gga | gag | tcc | ttc | cag | agc | agc | tgc | aag | tac | cag | tgc | acg | 505 |
| Tyr | Arg | Ser | Gly | Glu | Ser | Phe | Gln | Ser | Ser | Cys | Lys | Tyr | Gln | Cys | Thr | |
| 110 | | | | | 115 | | | | | 120 | | | | | 125 | |
| tgc | ctg | gac | ggg | gcg | gtg | ggc | tgc | atg | ccc | ctg | tgc | agc | atg | gac | gtt | 553 |
| Cys | Leu | Asp | Gly | Ala | Val | Gly | Cys | Met | Pro | Leu | Cys | Ser | Met | Asp | Val | |
| | | | 130 | | | | | 135 | | | | | 140 | | | |
| cgt | ctg | ccc | agc | cct | gac | tgc | ccc | ttc | ccg | agg | agg | gtc | aag | ctg | ccc | 601 |
| Arg | Leu | Pro | Ser 145 | Pro | Asp | Cys | Pro 150 | Phe | Pro | Arg | Arg | Val 155 | Lys | Leu | Pro | |
| ggg | aaa | tgc | tgc | gag | gag | tgg | gtg | tgt | gac | gag | ccc | aag | gac | caa | acc | 649 |
| Gly | Lys | Cys | Cys 160 | Glu | Glu | Trp | Val 165 | Cys | Asp | Glu | Pro | Lys 170 | Asp | Gln | Thr | |
| gtg | gtt | ggg | cct | gcc | ctc | gcg | gct | tac | cga | ctg | gaa | gac | acg | ttt | ggc | 697 |
| Val | Val | Gly | Pro 175 | Ala | Leu | Ala | Ala 180 | Tyr | Arg | Leu | Glu | Asp 185 | Thr | Phe | Gly | |
| cca | gac | cca | act | atg | att | aga | gcc | aac | tgc | ctg | gtc | cag | acc | aca | gag | 745 |
| Pro | Asp | Pro | Thr | Met | Ile | Arg | Ala | Asn | Cys | Leu | Val | Gln | Thr | Thr | Glu | |
| 190 | | | | | 195 | | | | | 200 | | | | | 205 | |
| tgg | agc | gcc | tgt | tcc | aag | acc | tgt | ggg | atg | ggc | atc | tcc | acc | cgg | gtt | 793 |
| Trp | Ser | Ala | Cys | Ser | Lys | Thr | Cys | Gly | Met | Gly | Ile | Ser | Thr | Arg | Val | |
| | | | 210 | | | | | 215 | | | | | 220 | | | |
| acc | aat | gac | aac | gcc | tcc | tgc | agg | cta | gag | aag | cag | agc | cgc | ctg | tgc | 841 |
| Thr | Asn | Asp | Asn | Ala | Ser | Cys | Arg | Leu | Glu | Lys | Gln | Ser | Arg | Leu | Cys | |
| | | | 225 | | | | | 230 | | | | | 235 | | | |
| atg | gtc | agg | cct | tgc | gaa | gct | gac | ctg | gaa | gag | aac | att | aag | aag | ggc | 889 |
| Met | Val | Arg | Pro 240 | Cys | Glu | Ala | Asp 245 | Leu | Glu | Glu | Asn | Ile 250 | Lys | Lys | Gly | |
| aaa | aag | tgc | atc | cgt | act | ccc | aaa | atc | tcc | aag | cct | atc | aag | ttt | gag | 937 |
| Lys | Lys | Cys | Ile 255 | Arg | Thr | Pro | Lys 260 | Ile | Ser | Lys | Pro | Ile 265 | Lys | Phe | Glu | |
| ctt | tct | ggc | tgc | acc | agc | atg | aag | aca | tac | cga | gct | aaa | ttc | tgt | gga | 985 |
| Leu | Ser | Gly | Cys | Thr | Ser | Met | Lys | Thr | Tyr | Arg | Ala | Lys | Phe | Cys | Gly | |
| 270 | | | | | 275 | | | | | 280 | | | | | 285 | |
| gta | tgt | acc | gac | ggc | cga | tgc | tgc | acc | ccc | cac | aga | acc | acc | acc | ctg | 1033 |
| Val | Cys | Thr | Asp | Gly | Arg | Cys | Cys | Thr | Pro | His | Arg | Thr | Thr | Thr | Leu | |
| | | | 290 | | | | | 295 | | | | | 300 | | | |
| ccg | gtg | gag | ttc | aag | tgc | cct | gac | ggc | gag | gtc | atg | aag | aag | aac | atg | 1081 |
| Pro | Val | Glu | Phe 305 | Lys | Cys | Pro | Asp 310 | Gly | Glu | Val | Met | Lys 315 | Lys | Asn | Met | |
| atg | ttc | atc | aag | acc | tgt | gcc | tgc | cat | tac | aac | tgt | ccc | gga | gac | aat | 1129 |
| Met | Phe | Ile | Lys 320 | Thr | Cys | Ala | Cys 325 | His | Tyr | Asn | Cys | Pro 330 | Gly | Asp | Asn | |
| gac | atc | ttt | gaa | tcg | ctg | tac | tac | agg | aag | atg | tac | gga | gac | atg | gca | 1177 |
| Asp | Ile | Phe | Glu 335 | Ser | Leu | Tyr | Tyr 340 | Arg | Lys | Met | Tyr | Gly 345 | Asp | Met | Ala | |
| tga agccagagag tgagagacat taactcatta gactggaact tgaactgatt | | | | | | | | | | | | | | | | 1230 |
| cacatctcat ttttccgtaa aaatgatttc agtagcacaa gttatttaaa tctgttttc | | | | | | | | | | | | | | | | 1290 |

```
taactgggggg aaaagattcc cacccaattc aaaacattgt gccatgtcaa acaaatagtc      1350
tatcaacccc agacactggt ttgaagaatg ttaagacttg acagtggaac tacattagta      1410
cacagcacca gaatgtatat taaggtgtgg ctttaggagc agtgggaggg taccagcaga      1470
aaggttagta tcatcagata gcatcttata cgagtaatat gcctgctatt tgaagtgtaa      1530
ttgagaagga aaattttagc gtgctcactg acctgcctgt agccccagtg acagctagga      1590
tgtgcattct ccagccatca agagactgag tcaagttgtt ccttaagtca gaacagcaga      1650
ctcagctctg acattctgat tcgaatgaca ctgttcagga tcggaatcc tgtcgattag       1710 actggacagc ttgtggcaag tgaatttgcc tgtaacaagc cagatttttt aaaatttata     1770
ttgtaaatat tgtgtgtgtg tgtgtgtgtg tatatatata tatatgtaca gttatctaag    1830
ttaatttaaa gttgtttgtg cctttttatt tttgttttta atgctttgat atttcaatgt     1890
tagcctcaat ttctgaacac cataggtaga atgtaaagct tgtctgatcg ttcaaagcat     1950
gaaatggata cttatatgga aattctgctc agatagaatg acagtccgtc aaaacagatt     2010
gtttgcaaag gggaggcatc agtgtccttg gcaggctgat ttctaggtag gaaatgtggt    2070
agcctcac                                                              2078
```

<210> SEQ ID NO 22
<211> LENGTH: 349
<212> TYPE: PRT
<213> ORGANISM: Homo sapiens

<400> SEQUENCE: 22

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220
```

```
Asn Ala Ser Cys Arg Leu Glu Lys Gln Ser Arg Leu Cys Met Val Arg
225                 230                 235                 240

Pro Cys Glu Ala Asp Leu Glu Asn Ile Lys Lys Gly Lys Lys Cys
            245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Leu Pro Val Glu
290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 23
<211> LENGTH: 2280
<212> TYPE: DNA
<213> ORGANISM: Homo sapiens
<220> FEATURE:
<221> NAME/KEY: CDS
<222> LOCATION: (143)..(1192)

<400> SEQUENCE: 23
gacggcagcc gccccggccg acagccccga gacgacagcc cggcgcgtcc cggtccccac     60
ctccgaccac cgccagcgct ccaggccccg ccgctcccg ctcgccgcca ccgcgccctc    120
cgctccgccc gcagtgccaa cc atg acc gcc gcc agt atg ggc ccc gtc cgc    172
                          Met Thr Ala Ala Ser Met Gly Pro Val Arg
                            1               5                  10 gtc gcc ttc gtg gtc ctc ctc gcc ctc tgc agc cgg ccg gcc gtc ggc    220
Val Ala Phe Val Val Leu Leu Ala Leu Cys Ser Arg Pro Ala Val Gly
            15                  20                  25 cag aac tgc agc ggg ccg tgc cgg tgc ccg gac gag ccg gcg ccg cgc    268
Gln Asn Cys Ser Gly Pro Cys Arg Cys Pro Asp Glu Pro Ala Pro Arg
        30                  35                  40 tgc ccg gcg ggc gtg agc ctc gtg ctg gac ggc tgc ggc tgc tgc cgc    316
Cys Pro Ala Gly Val Ser Leu Val Leu Asp Gly Cys Gly Cys Cys Arg
    45                  50                  55 gtc tgc gcc aag cag ctg ggc gag ctg tgc acc gag cgc gac cca tgc    364
Val Cys Ala Lys Gln Leu Gly Glu Leu Cys Thr Glu Arg Asp Pro Cys
60                  65                  70 gac ccg cac aag ggc cta ttc tgt cac ttc ggc tcc ccg gcc aac cgc    412
Asp Pro His Lys Gly Leu Phe Cys His Phe Gly Ser Pro Ala Asn Arg
75                  80                  85                  90 aag atc ggc gtg tgc acc gcc aaa gat ggt gct ccc tgc atc ttc ggt    460
Lys Ile Gly Val Cys Thr Ala Lys Asp Gly Ala Pro Cys Ile Phe Gly
                95                  100                 105 ggt acg gtg tac cgc agc gga gag tcc ttc cag agc agc tgc aag tac    508
Gly Thr Val Tyr Arg Ser Gly Glu Ser Phe Gln Ser Ser Cys Lys Tyr
            110                 115                 120 cag tgc acg tgc ctg gac ggg gcg gtg ggc tgc atg ccc ctg tgc agc    556
Gln Cys Thr Cys Leu Asp Gly Ala Val Gly Cys Met Pro Leu Cys Ser
        125                 130                 135 atg gac gtt cgt ctg ccc agc cct gac tgc ccc ttc ccg agg agg gtc    604
Met Asp Val Arg Leu Pro Ser Pro Asp Cys Pro Phe Pro Arg Arg Val
    140                 145                 150
```

-continued

```
aag ctg ccc ggg aaa tgc tgc gag gag tgg gtg tgt gac gag ccc aag      652
Lys Leu Pro Gly Lys Cys Cys Glu Glu Trp Val Cys Asp Glu Pro Lys
155                 160                 165                 170 gac caa acc gtg gtt ggg cct gcc ctc gcg gct tac cga ctg gaa gac      700
Asp Gln Thr Val Val Gly Pro Ala Leu Ala Ala Tyr Arg Leu Glu Asp
                175                 180                 185 acg ttt ggc cca gac cca act atg att aga gcc aac tgc ctg gtc cag      748
Thr Phe Gly Pro Asp Pro Thr Met Ile Arg Ala Asn Cys Leu Val Gln
            190                 195                 200 acc aca gag tgg agc gcc tgt tcc aag acc tgt ggg atg ggc atc tcc      796
Thr Thr Glu Trp Ser Ala Cys Ser Lys Thr Cys Gly Met Gly Ile Ser
        205                 210                 215 acc cgg gtt acc aat gac aac gcc tcc tgc agg cta gag aag cag agc      844
Thr Arg Val Thr Asn Asp Asn Ala Ser Cys Arg Leu Glu Lys Gln Ser
    220                 225                 230 cgc ctg tgc atg gtc agg cct tgc gaa gct gac ctg gaa gag aac att      892
Arg Leu Cys Met Val Arg Pro Cys Glu Ala Asp Leu Glu Glu Asn Ile
235                 240                 245                 250 aag aag ggc aaa aag tgc atc cgt act ccc aaa atc tcc aag cct atc      940
Lys Lys Gly Lys Lys Cys Ile Arg Thr Pro Lys Ile Ser Lys Pro Ile
                255                 260                 265 aag ttt gag ctt tct ggc tgc acc agc atg aag aca tac cga gct aaa      988
Lys Phe Glu Leu Ser Gly Cys Thr Ser Met Lys Thr Tyr Arg Ala Lys
            270                 275                 280 ttc tgt gga gta tgt acc gac ggc cga tgc tgc acc ccc cac aga acc      1036
Phe Cys Gly Val Cys Thr Asp Gly Arg Cys Cys Thr Pro His Arg Thr
        285                 290                 295 acc acc ctg ccg gtg gag ttc aag tgc cct gac ggc gag gtc atg aag      1084
Thr Thr Leu Pro Val Glu Phe Lys Cys Pro Asp Gly Glu Val Met Lys
    300                 305                 310 aag aac atg atg ttc atc aag acc tgt gcc tgc cat tac aac tgt ccc      1132
Lys Asn Met Met Phe Ile Lys Thr Cys Ala Cys His Tyr Asn Cys Pro
315                 320                 325                 330 gga gac aat gac atc ttt gaa tcg ctg tac tac agg aag atg tac gga      1180
Gly Asp Asn Asp Ile Phe Glu Ser Leu Tyr Tyr Arg Lys Met Tyr Gly
                335                 340                 345 gac atg gca tga agccagagag tgagagacat taactcatta gactggaact          1232
Asp Met Ala tgaactgatt cacatctcat ttttccgtaa aaatgatttc agtagcacaa gttatttaaa    1292 tctgttttc taactggggg aaaagattcc cacccaattc aaaacattgt gccatgtcaa    1352
acaaatagtc tatcaacccc agacactggt ttgaagaatg ttaagacttg acagtggaac    1412
tacattagta cacagcacca gaatgtatat taaggtgtgg ctttaggagc agtgggaggg    1472
taccagcaga aaggttagta tcatcagata gcatcttata cgagtaatat gcctgctatt    1532
tgaagtgtaa ttgagaagga aaattttagc gtgctcactg acctgcctgt agccccagtg    1592
acagctagga tgtgcattct ccagccatca agagactgag tcaagttgtt ccttaagtca    1652
gaacagcaga ctcagctctg acattctgat tcgaatgaca ctgttcagga atcggaatcc    1712
tgtcgattag actggacagc ttgtggcaag tgaatttgcc tgtaacaagc cagattttt    1772 aaaatttata ttgtaaatat tgtgtgtgtg tgtgtgtgtg tatatatata tatatgtaca    1832
gttatctaag ttaatttaaa gttgtttgtg cctttttatt tttgtttta atgctttgat    1892 atttcaatgt tagcctcaat ttctgaacac cataggtaga atgtaaagct tgtctgatcg    1952
ttcaaagcat gaaatggata cttatatgga aattctgctc agatagaatg acagtccgtc    2012
aaaacagatt gtttgcaaag gggaggcatc agtgtccttg gcaggctgat ttctaggtag    2072
```

```
gaaatgtggt agcctcactt ttaatgaaca aatggccttt attaaaaact gagtgactct    2132
atatagctga tcagttttt cacctggaag catttgtttc tactttgata tgactgtttt    2192
tcggacagtt tatttgttga gagtgtgacc aaaagttaca tgtttgcacc tttctagttg    2252
aaaataaagt gtatattttt tctataaa                                       2280
```

```
<210> SEQ ID NO 24
<211> LENGTH: 349
<212> TYPE: PRT
<213> ORGANISM: Homo sapiens

<400> SEQUENCE: 24
```

| | | | | | | | | | | | | | | | |
|---|---|---|---|---|---|---|---|---|---|---|---|---|---|---|---|
| Met | Thr | Ala | Ala | Ser | Met | Gly | Pro | Val | Arg | Val | Ala | Phe | Val | Val | Leu |
| 1 | | | | 5 | | | | | 10 | | | | | 15 | |

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

```
Glu Ser Leu Tyr Tyr Arg Lys Met Tyr Gly Asp Met Ala
        340                 345
```

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gcagttggct ctaatcatag                                           20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tgaccatgca caggcggctc                                           20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ctcaaacttg ataggcttgg                                           20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tttagctcgg tatgtcttca                                           20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cttgaactcc accggcaggg                                           20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
ggtcttgatg aacatcatgt                                           20

<210> SEQ ID NO 31
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 31
gacagttgta atggcaggca                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ccgtacatct tcctgtagta                                                   20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ccagctgctt ggcgcagacg                                                   20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
tctggaccag gcagttggct                                                   20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tgtggtctgg accaggcagt                                                   20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
cactctgtgg tctggaccag                                                   20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gatgcacttt ttgcccttct                                                   20
```

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gccagaaagc tcaaacttga                                          20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gtgcagccag aaagctcaaa                                          20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
caggtcttga tgaacatcat                                          20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
aggcacaggt cttgatgaac                                          20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
atggcaggca caggtcttga                                          20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
acagttgtaa tggcaggcac                                          20

<210> SEQ ID NO 44
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 44
ccacaagctg tccagtctaa                                                    20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
acttgccaca agctgtccag                                                    20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ttaacttaga taactgtaca                                                    20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ttaaattaac ttagataact                                                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ttaataaagg ccatttgttc                                                    20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cactctcaac aaataaactg                                                    20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ggtcacactc tcaacaaata                                                    20
```

```
<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
cttttggtca cactctcaac                                                 20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tgtaactttt ggtcacactc                                                 20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
aaacatgtaa cttttggtca                                                 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ctttattttc aactagaaag                                                 20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
cagctgcttg gcgcagacgc                                                 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ccttgggctc gtcacacacc                                                 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 57
tctgtggtct ggaccaggca                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cagccagaaa gctcaaactt                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ctggtgcagc cagaaagctc                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
acaggtcttg atgaacatca                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gcaggcacag gtcttgatga                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
taatggcagg cacaggtctt                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ccatgtctcc gtacatcttc                                              20

<210> SEQ ID NO 64
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 64
cttgccacaa gctgtccagt                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
aaaaatctgg cttgttacag                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ctttaaatta acttagataa                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tttggtcaca ctctcaacaa                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
gtaacttttg gtcacactct                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
caaacatgta acttttggtc                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
```
actttatttt caactagaaa        20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
cggcggtcat ggttggcact        20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
cccatactgg cggcggtcat        20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ccgtccagca cgaggctcac        20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
agaggccctt gtgcgggtcg        20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gagccgaagt cacagaagag        20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
aaggactctc cgctgcggta        20

<210> SEQ ID NO 77
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 77
cacgtgcact ggtacttgca                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
tcgcagcatt tcccgggcag                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ctcctcgcag catttcccgg                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gggctcgtca cacccact                                                 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gtctgggcca aacgtgtctt                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tctaatcata gttgggtctg                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
gaccaggcag ttggctctaa                                               20
```

```
<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ctctagcctg caggaggcgt                                                    20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
atgttctctt ccaggtcagc                                                    20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ggagattttg ggagtacgga                                                    20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ttgataggct tggagatttt                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
cacagaattt agctcggtat                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ggccgtcggt acatactcca                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 90
tccaccggca gggtggtggt                    20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
cagggcactt gaactccacc                    20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
ccgtcagggc acttgaactc                    20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
ggacagttgt aatggcaggc                    20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gtagtacagc gattcaaaga                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tctggcttca tgccatgtct                    20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tctctcactc tctggcttca                    20

<210> SEQ ID NO 97

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
tacggaaaaa tgagatgtga                                               20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
atttaaataa cttgtgctac                                               20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttcttcaaac cagtgtctgg                                               20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
cagtgagcac gctaaaattt                                               20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gttctgactt aaggaacaac                                               20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
gctgtccagt ctaatcgaca                                               20

<210> SEQ ID NO 103
<211> LENGTH: 2330
<212> TYPE: DNA
<213> ORGANISM: Mus musculus
<220> FEATURE:
<221> NAME/KEY: CDS
<222> LOCATION: (204)..(1250)
```

<400> SEQUENCE: 103

```
agactcagcc agatccactc cagctccgac cccaggagac cgacctcctc cagacggcag      60
cagccccagc ccagccgaca accccagacg ccaccgcctg gagcgtccag acaccaacct     120
ccgcccctgt ccgaatccag gctccagccg cgcctctcgt cgcctctgca ccctgctgtg     180
catcctccta ccgcgtcccg atc atg ctc gcc tcc gtc gca ggt ccc atc agc    233
               Met Leu Ala Ser Val Ala Gly Pro Ile Ser
               1               5                   10 ctc gcc ttg gtg ctc ctc gcc ctc tgc acc cgg cct gct acg ggc cag      281
Leu Ala Leu Val Leu Leu Ala Leu Cys Thr Arg Pro Ala Thr Gly Gln
                15                  20                  25 gac tgc agc gcg caa tgt cag tgc gca gcc gaa gca gcg ccg cac tgc      329
Asp Cys Ser Ala Gln Cys Gln Cys Ala Ala Glu Ala Ala Pro His Cys
        30                  35                  40 ccc gcc ggc gtg agc ctg gtg ctg gac ggc tgc ggc tgc tgc cgc gtc      377
Pro Ala Gly Val Ser Leu Val Leu Asp Gly Cys Gly Cys Cys Arg Val
    45                  50                  55 tgc gcc aag cag ctg gga gaa ctg tgt acg gag cgt gac ccc tgc gac      425
Cys Ala Lys Gln Leu Gly Glu Leu Cys Thr Glu Arg Asp Pro Cys Asp
60                  65                  70 cca cac aag ggc ctc ttc tgc gat ttc ggc tcc ccc gcc aac cgc aag      473
Pro His Lys Gly Leu Phe Cys Asp Phe Gly Ser Pro Ala Asn Arg Lys
75                  80                  85                  90 att gga gtg tgc act gcc aaa gat ggt gca ccc tgt gtc ttc ggt ggg      521
Ile Gly Val Cys Thr Ala Lys Asp Gly Ala Pro Cys Val Phe Gly Gly
                95                  100                 105 tcg gtg tac cgc agc ggt gag tcc ttc caa agc agc tgc aaa tac caa      569
Ser Val Tyr Arg Ser Gly Glu Ser Phe Gln Ser Ser Cys Lys Tyr Gln
        110                 115                 120 tgc act tgc ctg gat ggg gcc gtg ggc tgc gtg ccc cta tgc agc atg      617
Cys Thr Cys Leu Asp Gly Ala Val Gly Cys Val Pro Leu Cys Ser Met
    125                 130                 135 gac gtg cgc ctg ccc agc cct gac tgc ccc ttc ccg aga agg gtc aag      665
Asp Val Arg Leu Pro Ser Pro Asp Cys Pro Phe Pro Arg Arg Val Lys
140                 145                 150 ctg cct ggg aaa tgc tgc gag gag tgg gtg tgt gac gag ccc aag gac      713
Leu Pro Gly Lys Cys Cys Glu Glu Trp Val Cys Asp Glu Pro Lys Asp
155                 160                 165                 170 cgc aca gca gtt ggc cct gcc cta gct gcc tac cga ctg gaa gac aca      761
Arg Thr Ala Val Gly Pro Ala Leu Ala Ala Tyr Arg Leu Glu Asp Thr
                175                 180                 185 ttt ggc cca gac cca act atg atg cga gcc aac tgc ctg gtc cag acc      809
Phe Gly Pro Asp Pro Thr Met Met Arg Ala Asn Cys Leu Val Gln Thr
        190                 195                 200 aca gag tgg agc gcc tgt tct aag acc tgt gga atg ggc atc tcc acc      857
Thr Glu Trp Ser Ala Cys Ser Lys Thr Cys Gly Met Gly Ile Ser Thr
    205                 210                 215 cga gtt acc aat gac aat acc ttc tgc aga ctg gag aag cag agc cgc      905
Arg Val Thr Asn Asp Asn Thr Phe Cys Arg Leu Glu Lys Gln Ser Arg
220                 225                 230 ctc tgc atg gtc agg ccc tgc gaa gct gac ctg gag gaa aac att aag      953
Leu Cys Met Val Arg Pro Cys Glu Ala Asp Leu Glu Glu Asn Ile Lys
235                 240                 245                 250 aag ggc aaa aag tgc atc cgg aca cct aaa atc gcc aag cct gtc aag     1001
Lys Gly Lys Lys Cys Ile Arg Thr Pro Lys Ile Ala Lys Pro Val Lys
                255                 260                 265 ttt gag ctt tct ggc tgc acc agt gtg aag aca tac agg gct aag ttc     1049
Phe Glu Leu Ser Gly Cys Thr Ser Val Lys Thr Tyr Arg Ala Lys Phe
        270                 275                 280
```

-continued

| | | |
|---|---|---|
| tgc ggg gtg tgc aca gac ggc cgc tgc tgc aca ccg cac aga acc acc<br>Cys Gly Val Cys Thr Asp Gly Arg Cys Cys Thr Pro His Arg Thr Thr<br>           285                 290                 295 | | 1097 |
| act ctg cca gtg gag ttc aaa tgc ccc gat ggc gag atc atg aaa aag<br>Thr Leu Pro Val Glu Phe Lys Cys Pro Asp Gly Glu Ile Met Lys Lys<br>300                 305                 310 | | 1145 |
| aat atg atg ttc atc aag acc tgt gcc tgc cat tac aac tgt cct ggg<br>Asn Met Met Phe Ile Lys Thr Cys Ala Cys His Tyr Asn Cys Pro Gly<br>315                 320                 325                 330 | | 1193 |
| gac aat gac atc ttt gag tcc ctg tac tac agg aag atg tac gga gac<br>Asp Asn Asp Ile Phe Glu Ser Leu Tyr Tyr Arg Lys Met Tyr Gly Asp<br>           335                 340                 345 | | 1241 |
| atg gcg taa agccaggaag taagggacac gaactcatta gactataact<br>Met Ala | | 1290 |
| tgaactgagt tgcatctcat tttcttctgt aaaaacaatt acagtagcac attaatttaa | | 1350 |
| atctgtgttt ttaactaccg tgggaggaac tatcccacca aagtgagaac gttatgtcat | | 1410 |
| ggccatacaa gtagtctgtc aacctcagac actggtttcg agacagttta cacttgacag | | 1470 |
| ttgttcatta gcgcacagtg ccagaacgca cactgaggtg agtctcctgg aacagtggag | | 1530 |
| atgccaggag aaagaaagac aggtactagc tgaggttatt ttaaaagcag cagtgtgcct | | 1590 |
| acttttttgga gtgtaaccgg ggagggaaat tatagcatgc ttgcagacag acctgctcta | | 1650 |
| gcgagagctg agcatgtgtc ctccactaga tgaggctgag tccagctgtt ctttaagaac | | 1710 |
| agcagtttca gctctgacca ttctgattcc agtgacactt gtcaggagtc agagccttgt | | 1770 |
| ctgttagact ggacagcttg tggcaagtaa gtttgcctgt aacaagccag attttattg | | 1830 |
| atattgtaaa tattgtggat atatatatat atatatatat atttgtacag ttatctaagt | | 1890 |
| taatttaaag tcatttgttt ttgttttaag tgcttttggg attttaaact gatagcctca | | 1950 |
| aactccaaac accataggta ggacacgaag cttatctgtg attcaaaaca aaggagatac | | 2010 |
| tgcagtggga attgtgacct gagtgactct ctgtcagaac aaacaaatgc tgtgcaggtg | | 2070 |
| ataaagctat gtattggaag tcagatttct agtaggaaat gtggtcaaat ccctgttggt | | 2130 |
| gaacaaatgg cctttattaa gaaatggctg gctcagggta aggtccgatt cctaccagga | | 2190 |
| agtgcttgct gcttctttga ttatgactgg tttggggtgg ggggcagttt atttgttgag | | 2250 |
| agtgtgacca aaagttacat gtttgcactt tctagttgaa aataaagtat atatatattt | | 2310 |
| ttatatgaaa aaaaaaaaa | | 2330 |

<210> SEQ ID NO 104
<211> LENGTH: 348
<212> TYPE: PRT
<213> ORGANISM: Mus musculus

<400> SEQUENCE: 104

Met Leu Ala Ser Val Ala Gly Pro Ile Ser Leu Ala Leu Val Leu Leu
1               5                    10                  15

Ala Leu Cys Thr Arg Pro Ala Thr Gly Gln Asp Cys Ser Ala Gln Cys
           20                    25                    30

Gln Cys Ala Ala Glu Ala Ala Pro His Cys Pro Ala Gly Val Ser Leu
           35                    40                    45

Val Leu Asp Gly Cys Gly Cys Cys Arg Val Cys Ala Lys Gln Leu Gly
      50                   55                    60

Glu Leu Cys Thr Glu Arg Asp Pro Cys Asp Pro His Lys Gly Leu Phe
65               70                    75                  80

```
Cys Asp Phe Gly Ser Pro Ala Asn Arg Lys Ile Gly Val Cys Thr Ala
                85                  90                  95
Lys Asp Gly Ala Pro Cys Val Phe Gly Gly Ser Val Tyr Arg Ser Gly
            100                 105                 110
Glu Ser Phe Gln Ser Ser Cys Lys Tyr Gln Cys Thr Cys Leu Asp Gly
        115                 120                 125
Ala Val Gly Cys Val Pro Leu Cys Ser Met Asp Val Arg Leu Pro Ser
    130                 135                 140
Pro Asp Cys Pro Phe Pro Arg Arg Val Lys Leu Pro Gly Lys Cys Cys
145                 150                 155                 160
Glu Glu Trp Val Cys Asp Glu Pro Lys Asp Arg Thr Ala Val Gly Pro
                165                 170                 175
Ala Leu Ala Ala Tyr Arg Leu Glu Asp Thr Phe Gly Pro Asp Pro Thr
            180                 185                 190
Met Met Arg Ala Asn Cys Leu Val Gln Thr Thr Glu Trp Ser Ala Cys
        195                 200                 205
Ser Lys Thr Cys Gly Met Gly Ile Ser Thr Arg Val Thr Asn Asp Asn
    210                 215                 220
Thr Phe Cys Arg Leu Glu Lys Gln Ser Arg Leu Cys Met Val Arg Pro
225                 230                 235                 240
Cys Glu Ala Asp Leu Glu Glu Asn Ile Lys Lys Gly Lys Lys Cys Ile
                245                 250                 255
Arg Thr Pro Lys Ile Ala Lys Pro Val Lys Phe Glu Leu Ser Gly Cys
            260                 265                 270
Thr Ser Val Lys Thr Tyr Arg Ala Lys Phe Cys Gly Val Cys Thr Asp
        275                 280                 285
Gly Arg Cys Cys Thr Pro His Arg Thr Thr Thr Leu Pro Val Glu Phe
    290                 295                 300
Lys Cys Pro Asp Gly Glu Ile Met Lys Lys Asn Met Met Phe Ile Lys
305                 310                 315                 320
Thr Cys Ala Cys His Tyr Asn Cys Pro Gly Asp Asn Asp Ile Phe Glu
                325                 330                 335
Ser Leu Tyr Tyr Arg Lys Met Tyr Gly Asp Met Ala
            340                 345

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105 acttttttgcc cttcttaatg                                            20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gacgctccag gcggtggcgt                                             20

<210> SEQ ID NO 107
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 107
gtctggacgc tccaggcggt                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
cggctggagc ctggattcgg                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
gagaggcgcg gctggagcct                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
acgcggtagg aggatgcaca                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
gaggcgagca tgatcgggac                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
ggcgcagacg cggcagcagc                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
tgcttggcgc agacgcggca                                               20
```

```
<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gcccttgtgt gggtcgcagg                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
aatcgcagaa gaggcccttg                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
accgacccac cgaagacaca                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
ttggtatttg cagctgcttt                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
cacgcagccc acggccccat                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
gcacgtccat gctgcatagg                                              20

<210> SEQ ID NO 120
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 120
gcagcttgac ccttctcggg                                                    20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
actgctgtgc ggtccttggg                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
gtgtcttcca gtcggtaggc                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
aaggtattgt cattggtaac                                                    20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
ggctctgctt ctccagtctg                                                    20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
tcttcacact ggtgcagcca                                                    20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
cgtctgtgca cacccgcag                                                     20
```

```
<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
cggtgtgcag cagcggccgt                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
tccactggca gagtggtggt                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
catcatattc tttttcatga                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
gtcattgtcc ccaggacagt                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
tcctggcttt acgccatgtc                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
aaatgagatg caactcagtt                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 133
tcagtgtgcg ttctggcact                                        20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
gttccaggag actcacctca                                        20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tctccactgt tccaggagac                                        20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
tctcctggca tctccactgt                                        20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tttctttctc ctggcatctc                                        20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
tccccggtta cactccaaaa                                        20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
aggtctgtct gcaagcatgc                                        20

<210> SEQ ID NO 140
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 140
tgctcagctc tcgctagagc                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
agtgtcactg gaatcagaat                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
caaatatata tatatatata                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
acttaaaaca aaacaaatg                                               20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
gctatcagtt taaaatccca                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
gtgtcctacc tatggtgttt                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146

-continued tttgaatcac agataagctt 20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
cagtatctcc tttgttttga 20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
attcccactg cagtatctcc 20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
caggtcacaa ttcccactgc 20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
ctgacagaga gtcactcagg 20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gctttatcac ctgcacagca 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
tacatagctt tatcacctgc 20

<210> SEQ ID NO 153
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 153
cttccaatac atagctttat                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
tctgacttcc aatacatagc                                               20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
atttgttcac caacagggat                                               20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
ttaccctgag ccagccattt                                               20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
aagaagcagc aagcacttcc                                               20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
cagtcataat caaagaagca                                               20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
atatacttta ttttcaacta                                               20
```

<210> SEQ ID NO 160
<211> LENGTH: 18
<212> TYPE: DNA
<213> ORGANISM: Artificial Sequence
<220> FEATURE:
<223> OTHER INFORMATION: PCR Primer

<400> SEQUENCE: 160
aaacggaagc gcactgaa                                                 18

<210> SEQ ID NO 161
<211> LENGTH: 20
<212> TYPE: DNA
<213> ORGANISM: Artificial Sequence
<220> FEATURE:
<223> OTHER INFORMATION: PCR Primer

<400> SEQUENCE: 161
gggactggcg agccttagtt                                               20

<210> SEQ ID NO 162
<211> LENGTH: 21
<212> TYPE: DNA
<213> ORGANISM: Artificial Sequence
<220> FEATURE:
<223> OTHER INFORMATION: PCR Probe

<400> SEQUENCE: 162
ccatccgtgg ccagatcctg t                                             21

<210> SEQ ID NO 163
<211> LENGTH: 18
<212> TYPE: DNA
<213> ORGANISM: Artificial Sequence
<220> FEATURE:
<223> OTHER INFORMATION: PCR Primer

<400> SEQUENCE: 163
ccgtccatcg agctgacc                                                 18

<210> SEQ ID NO 164
<211> LENGTH: 19
<212> TYPE: DNA
<213> ORGANISM: Artificial Sequence
<220> FEATURE:
<223> OTHER INFORMATION: PCR Primer

<400> SEQUENCE: 164
tgcaacgtct tcattcttc                                                19

<210> SEQ ID NO 165
<211> LENGTH: 22
<212> TYPE: DNA
<213> ORGANISM: Artificial Sequence
<220> FEATURE:
<223> OTHER INFORMATION: PCR Probe

<400> SEQUENCE: 165
acctcttggt gcgctactca cc                                            22

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
ccacaagctg tccagtctaa                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
ccttccctga aggttcctcc                                              20

<210> SEQ ID NO 168
<211> LENGTH: 21
<212> TYPE: DNA
<213> ORGANISM: Artificial Sequence
<220> FEATURE:
<223> OTHER INFORMATION: PCR Primer

<400> SEQUENCE: 168
gctcagggta aggtccgatt c                                            21

<210> SEQ ID NO 169
<211> LENGTH: 15
<212> TYPE: DNA
<213> ORGANISM: Artificial Sequence
<220> FEATURE:
<223> OTHER INFORMATION: PCR Primer

<400> SEQUENCE: 169
gccccccacc ccaaa                                                   15

<210> SEQ ID NO 170
<211> LENGTH: 29
<212> TYPE: DNA
<213> ORGANISM: Artificial Sequence
<220> FEATURE:
<223> OTHER INFORMATION: PCR Probe

<400> SEQUENCE: 170
tcataatcaa agaagcagca agcacttcc                                    29

<210> SEQ ID NO 171
<211> LENGTH: 20
<212> TYPE: DNA
<213> ORGANISM: Artificial Sequence
<220> FEATURE:
<223> OTHER INFORMATION: PCR Primer

<400> SEQUENCE: 171
tggattcccg ttcgagtacg                                              20

<210> SEQ ID NO 172
<211> LENGTH: 20
<212> TYPE: DNA
<213> ORGANISM: Artificial Sequence
<220> FEATURE:
<223> OTHER INFORMATION: PCR Primer

<400> SEQUENCE: 172
tcagctggat agcgacatcg                                              20

<210> SEQ ID NO 173

-continued

```
<211> LENGTH: 20
<212> TYPE: DNA
<213> ORGANISM: Artificial Sequence
<220> FEATURE:
<223> OTHER INFORMATION: PCR Probe

<400> SEQUENCE: 173
aagcgagggc tccgacccga                                              20

<210> SEQ ID NO 174
<211> LENGTH: 22
<212> TYPE: DNA
<213> ORGANISM: Artificial Sequence
<220> FEATURE:
<223> OTHER INFORMATION: PCR Primer

<400> SEQUENCE: 174
agaccaacaa gcaagtgagt gc                                           22

<210> SEQ ID NO 175
<211> LENGTH: 24
<212> TYPE: DNA
<213> ORGANISM: Artificial Sequence
<220> FEATURE:
<223> OTHER INFORMATION: PCR Primer

<400> SEQUENCE: 175
ctagcatgtg agccacattc atcc                                         24

<210> SEQ ID NO 176
<211> LENGTH: 21
<212> TYPE: DNA
<213> ORGANISM: Artificial Sequence
<220> FEATURE:
<223> OTHER INFORMATION: PCR Probe

<400> SEQUENCE: 176
ctgctgaggg cacgctgagc t                                            21
```